(12) United States Patent
Yu et al.

(10) Patent No.: US 11,406,643 B2
(45) Date of Patent: Aug. 9, 2022

(54) TARGETING KINASES FOR THE TREATMENT OF CANCER METASTASIS

(71) Applicant: Board of Regents, The University of Texas System, Austin, TX (US)

(72) Inventors: Dihua Yu, Houston, TX (US); Frank Lowery, Houston, TX (US); Chenyu Zhang, Houston, TX (US); Sunil Acharya, Houston, TX (US); Ping Li, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/638,222

(22) PCT Filed: Aug. 10, 2018

(86) PCT No.: PCT/US2018/046329
§ 371 (c)(1),
(2) Date: Feb. 11, 2020

(87) PCT Pub. No.: WO2019/033041
PCT Pub. Date: Feb. 14, 2019

(65) Prior Publication Data
US 2020/0197407 A1    Jun. 25, 2020

Related U.S. Application Data

(60) Provisional application No. 62/544,597, filed on Aug. 11, 2017.

(51) Int. Cl.
| | | |
|---|---|---|
| *A61K 31/55* | (2006.01) |
| *A61P 35/04* | (2006.01) |
| *A61K 31/4025* | (2006.01) |
| *A61K 31/42* | (2006.01) |
| *A61K 31/427* | (2006.01) |
| *A61K 31/4439* | (2006.01) |
| *A61K 31/454* | (2006.01) |
| *A61K 31/4745* | (2006.01) |
| *A61K 31/52* | (2006.01) |
| *A61K 31/5377* | (2006.01) |
| *A61K 31/7105* | (2006.01) |
| *A61K 9/00* | (2006.01) |
| *A61K 45/06* | (2006.01) |

(52) U.S. Cl.
CPC .......... *A61K 31/55* (2013.01); *A61K 31/4025* (2013.01); *A61K 31/42* (2013.01); *A61K 31/427* (2013.01); *A61K 31/4439* (2013.01); *A61K 31/454* (2013.01); *A61K 31/4745* (2013.01); *A61K 31/52* (2013.01); *A61K 31/5377* (2013.01); *A61K 31/7105* (2013.01); *A61P 35/04* (2018.01); *A61K 9/0019* (2013.01); *A61K 9/0085* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,700,301 B2 | 4/2010 | Wood et al. |
| 8,101,176 B2 | 1/2012 | Kuchroo et al. |
| 9,333,256 B2 | 5/2016 | Kuchroo et al. |
| 9,370,551 B2 | 6/2016 | Cong et al. |
| 10,413,522 B2 * | 9/2019 | Massague | A61P 43/00 |
| 2010/0029748 A1 | 2/2010 | Massague et al. |
| 2010/0113297 A1 | 5/2010 | Lidereau et al. |
| 2016/0008366 A1 | 1/2016 | Sukbuntherng et al. |

FOREIGN PATENT DOCUMENTS

| | | | |
|---|---|---|---|
| WO | WO 2007/044571 | 4/2007 |
| WO | WO-2015011282 A2 * | 1/2015 | A61P 35/00 |
| WO | WO-2016024131 A1 * | 2/2016 | C07K 5/1016 |
| WO | WO-2016174183 A1 * | 11/2016 | A61K 31/454 |

OTHER PUBLICATIONS

Criscitiello et al., "Dinaciclib for the treatment of breast cancer", 2014, Expert Opinion on Investigational Drugs, 23(9), pp. 1305-1312. (DOI: 10.1517/13543784.2014.948152) (Year: 2014).*
Kritsanida et al., "Synthesis and Antiproliferative Activity of 7-Azaindirubin-3'-oxime, a 7-Aza Isostere of the Natural Indirubin Pharmacophore", 2009, Journal of Natural Products, 72(12), pp. 2199-2202. (Year: 2009).*
Zhao et al., "Novel Modeling of Cancer Cell Signaling Pathways Enables Systematic Drug Repositioning for Distinct Breast Cancer Metastases", 2013, The Journal of Cancer Research, 73(20), pp. 6149-6163. (Year: 2013).*
Van Swearingen et al., "Combined kinase inhibitors of MEK1/2 and either PI3K or PDGFR are efficacious in intracranial triple-negative breast cancer", 2017, Neuro-Oncology, 19(11), pp. 1481-1493. (doi:10.1093/neuonc/nox052) (Year: 2017).*
Lowery, "In vivo kinome screen reveals non-canonical CDK-driven metabolic adaptation in brain metastasis," Dissertation and Theses, pp. 1-169, 2016.
Patrial Supplementary European Search Report issued in European Application No. 18845216.3, dated Feb. 23, 2021.
"Protein kinase C, delta binding protein (PRKCDBP) ELISA kits," located at http://www.antibodies-online.com/abstract/protein+kinase+c,+delta+binding+protein+(PRKCDBP)+ELISA+kit/, 2016.
"Study of cabazitaxel in patients with metastatic breast cancer previously treated with taxanes," located at https://clinicaltrials.gov/ct2/show/NCT01693549, Clinical Trial, Hellenic Cooperative Oncology Group, Sanofi, 2016.

(Continued)

*Primary Examiner* — My-Chau T. Tran
(74) *Attorney, Agent, or Firm* — Parker Highlander PLLC

(57) ABSTRACT

Provided herein are methods for the treatment of brain metastasis by administering a kinase inhibitor targeted to a metastasis-promoting kinase identified by an in vivo kinase screen.

35 Claims, 10 Drawing Sheets

(56) References Cited

OTHER PUBLICATIONS

Acharya et al., "SPHK1 promotes lung metastasis of breast cancer," *Cancer Research*, Abstract 2010, Proceedings AACR Annual Meeting 2014.

Al-Ejeh et al., "Kinome profiling reveals breast cancer heterogeneity and identifies targeted therapeutic opportunities for triple negative breast cancer," *Oncotarget*, 5(10):3145-3158, 2014.

Boonsri et al., "Molecular docking and NMR binding studies to identify novel inhibitors of human phosphomevalonate kinase," *Biochem Biophys Res Commun.*, 430(1):313-319, 2013.

Ćwiek et al., "RNA interference screening identifies a novel role for PCTK1/CDK16 in medulloblastoma with c-Myc amplification," *Oncotarget*, 6(1):116-129, 2015.

Hong et al., "miR-125b inhibited epithelial-mesenchymal transition of triple-negative breast cancer by targeting MAP2K7," *OncoTargets and Therapy*, 9:2639-2648, 2016.

Lin et al., "The CaMKK2/CaMKIV relay is an essential regulator of hepatic cancer," *Hepatology*, 62(2):505-520, 2015.

Lowery et al., "Identification of novel targets in breast cancer brain metastasis," Abstract A91, 15th International Biennial Congress of the Metastasis Research Society, 2014.

Lowery, "In vivo kinome screen reveals non-canonical CDK-driven metabolic adaptation in brain metastasis," Dissertation Abstract, 2016.

Malami et al., "In Silico Discovery of Potential Uridine-Cytidine Kinase 2 Inhibitors from the Rhizome of Alpinia mutica," *Molecules*, 21(4):417, 2016.

PCT International Search Report and Written Opinion issued in International Application No. PCT/US2018/046329, dated Dec. 27, 2018.

Pozo and Bibb, "The emerging role of Cdk5 in cancer," *Trends in Cancer*, 2(10):606-618, 2016.

Rane, "In vivo efficacy of the PAK4 allosteric modulator KPT-9274 against a triple-negative breast cancer model," American Association for Cancer Research Annual Meeting, 2016.

Vander Griend et al., "Suppression of metastatic colonization by the context-dependent activation of the c-Jun $NH_2$-terminal kinase kinases JNKK1/MKK4 and MKK7," *Cancer Res.*, 65(23):10984-10991, 2005.

Wu et al., "Acalabrutinib (ACP-196): a selective second-generation BTK inhibitor," *Journal of Hematology & Oncology*, 9:21, 2016.

Xu et al., "Differential proteomic analysis of a highly metastatic variant of human breast cancer cells using two-dimensional differential gel electrophoresis," *J Cancer Res Clin Oncol*, 136:1545-1556, 2010.

\* cited by examiner

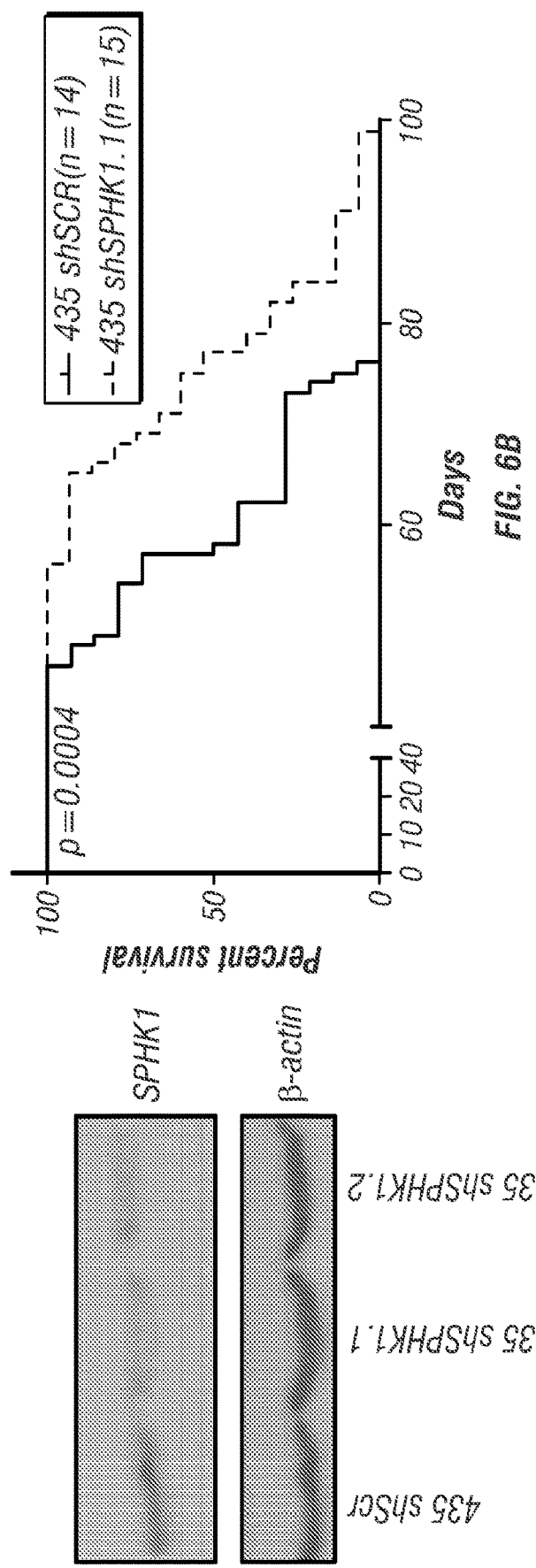

TARGETING KINASES FOR THE TREATMENT OF CANCER METASTASIS

The present application is a national phase application under 35 U.S.C. § 371 of International Application No. PCT/US2018/046329, filed Aug. 10, 2018, which claims the priority benefit of U.S. Provisional Application Ser. No. 62/544,597, filed Aug. 11, 2017, the entire contents of which are hereby incorporated by reference.

This invention was made with government support under grant numbers R01 CA112567 and R01 CA184836 awarded by the National Institutes of Health. The government has certain rights in the invention.

BACKGROUND

1. Field

The present invention relates generally to the fields of molecular biology and medicine. More particularly, it concerns methods of targeting kinases for the treatment of cancer, particularly brain metastasis.

2. Description of Related Art

Brain metastases affect millions of cancer patients and outnumber primary brain tumors by more than 10 to 1. Major neoplastic diseases (e.g., melanoma, lung, breast, and colon cancers) have high incidences of brain metastases. One year survival after diagnosis of brain metastasis is less than 20%. Recently, advances in targeted cancer therapies (e.g., trastuzumab, T-DM1) have prolonged patients' survival through better control of the systemic disease. However, when patients later have recurrences, they develop brain metastasis at an increasing rate (e.g., more than 30%), representing an emerging challenge in this era of successful targeted therapies. Current treatment options are limited and merely palliative for patients with brain metastasis.

Kinases, which constitute a large family of enzymes, catalyze the transfer of the γ-phosphate of ATP to protein substrates. Reversible phosphorylation plays a paramount role in cell signaling processes and is regulated by kinases and phosphatases. Accordingly, kinases are important mediators of a myriad of signal transduction processes. Aberrant kinase activity is linked to cancer as well as metabolic disorders, immunological disorders, nervous system disorders, and other disorders. As a result, kinases have emerged as an important class of drug targets for human disease.

Many kinases are the central nodes of cancer cell signaling networks. Numerous efforts have led to successful development of several FDA-approved inhibitors to various cancer-promoting kinases with remarkable clinical efficacy. These cancer promoting kinases have proven to be reliable drug targets in many disease settings, including: Trastuzumab (ErbB2), Lapatinib (ErbB2 and EGFR), Imatinib (BCR-Abl), Gefitinib (EGFR), Ibrutinib (BTK), and Vemurafenib (BRAF). However, most existing kinase inhibitors were developed based on targets in primary tumors; no efforts have been made to identify metastasis-specific, especially brain metastasis-specific, druggable molecular targets. Therefore, while the current FDA-approved inhibitors to various cancer-promoting kinases may show remarkable clinical efficacy in inhibiting primary tumors, they show little or no efficacy in inhibiting brain metastasis. Thus, to tackle the growing clinical challenge of brain metastasis, there is an unmet need to identify its drivers and therapeutically target them in order to prolong the survival and improve the quality of life of patients with brain metastasis.

SUMMARY

In a first embodiment, the present disclosure provides a method for inhibiting brain metastasis in a subject having a cancer comprising administering an effective amount of a kinase inhibitor to the subject, wherein the kinase inhibitor targets a kinase selected from the group consisting of ADCK4, BTK, CAMK4, CDK5, CDK5R1, CLK3, LIMK2, PAK4, PMVK, PRKACB, PRKACG, PRKCI, TSSK6, and ZC3HC1. In some aspects, the subject is human. In certain aspects, the kinase inhibitor is siRNA or miRNA. In other aspects, the kinase inhibitor is a selective pharmacological inhibitor.

In some aspects, the cancer is breast cancer. In particular aspects, the breast cancer is further defined as triple negative breast cancer. In other aspects, the cancer is lung cancer.

In certain aspects, the subject was not known to have brain metastasis prior to treatment. In other aspects, the subject was known to have one or more brain metastases prior to treatment.

In some aspects, the kinase inhibitor targets CDK5 or LIMK2. In certain aspects, the kinase inhibitor of CDK5 is dinaciclib, bis-indole indirubin, (S)-CR8, kenpaullone, PHA-793887, AT7519, roscovitine, milciclib, SNS-032, or olomoucine. In some aspects, the kinase inhibitor of LIMK2 is BMS-5, Pyr-1, or T56-LIMKi.

In some aspects, the kinase inhibitor of BTK is ibrutinib, acalabrutinib, ONO-4059, spebrutinib, BGB-3111, or HM71224. In certain aspects, the kinase inhibitor of CAMK4 is KN-93. In some aspects, the kinase inhibitor of MAP2K7 is DTP3. In some aspects, the kinase inhibitor of PMVK is CDDD_1633, CSDDD_2260, CSDDD_2419, or luteolin. In some aspects, the kinase inhibitor of PRKCI is ridaura or RXDX-108.

In some aspects, the kinase inhibitor is administered orally, topically, intravenously, intraperitoneally, intramuscularly, endoscopically, percutaneously, subcutaneously, regionally, or by direct injection. In specific aspects, the kinase inhibitor is administered intravenously. In particular aspects, the kinase inhibitor is delivered directly to the brain. In some aspects, the kinase inhibitor is administered intrathecally or intranasally.

In additional aspects, the method further comprises administering at least a second therapeutic agent. In some aspects, the second therapeutic agent is chemotherapy, radiotherapy, gene therapy, surgery, hormonal therapy, anti-angiogenic therapy or cytokine therapy. In particular aspects, the second therapeutic agent is radiation therapy, chemotherapy, immunotherapy, and/or metabolic modulation. In some aspects, the second therapeutic agent is administered concurrently with the kinase inhibitor. In certain aspects, the second therapeutic agent is administered sequentially with the kinase inhibitor.

In another embodiment, there is provided a method for treating brain metastasis in a subject having a cancer comprising administering an effective amount of a kinase inhibitor in combination with at least a second anti-cancer agent to the subject in need thereof, wherein the kinase inhibitor targets a kinase selected from the group consisting of PCTK1, SPHK1, FRK, MAPK12, ERK5, MAP2K7, UCK2, DAK, and PRKCD. In some aspects, the cancer is breast cancer. In particular aspects, the breast cancer is further defined as triple negative breast cancer. In other aspects, the cancer is lung cancer. In some aspects, the subject was not known to have brain metastasis prior to treatment. In other aspects, the subject was known to have one or more brain metastasis prior to treatment. In some aspects, the subject is human.

In particular aspects, the kinase inhibitor targets PCTK1, SPHK1, MAPK12, or CDK5. In some aspects, the kinase inhibitor of MAPK12 is SB 203580, doramapimod, or LY2228820. In certain aspects, the kinase inhibitor of PCTK1 is indirubin E804, dabrafenib, or rebastinib. In particular aspects, the kinase inhibitor of PCTK1 is rebastinib. In some aspects, the kinase inhibitor of SPHK1 is BML-258, SKI III, SKI 5C, MP A08, SKI 178, PF-543, fingolimod, or safingol. In particular aspects, the kinase inhibitor of SPHK1 is fingolimod or safingol. In some aspects, the kinase inhibitor of CDK5 is dinaciclib, PHA-793887, AT7519, CYC-065, rocovitine, or DCAM-422. In particular aspects, the kinase inhibitor of CDK5 is CYC-065 or DCAM-422.

In some aspects, the kinase inhibitor of ERK5 is ERK5-IN-1, BIX 02189, XMD17-109, or XMD 8-92. In certain aspects, the kinase inhibitor of FRK is dasatinib, motesanib, doramapimod, pelitinib, sorafenib, vandetanib, canertinib, or imatinib. In certain aspects, the kinase inhibitor of PAK4 is PF-3758309, LCH-7749944, glaucarubinone, KY-04031, KY-04045, 1-phenanthryl-tetrahydroisoquinoline derivatives, (–)-β-hydrastine, Inka1, GL-1196, or GNE-2861. In some aspects, the kinase inhibitor of UCK2 is flavokawain B or alpinetin.

In certain aspects, the kinase inhibitor is administered orally, topically, intravenously, intraperitoneally, intramuscularly, endoscopically, percutaneously, subcutaneously, regionally, or by direct injection. In particular aspects, the kinase inhibitor is administered intravenously. In some aspects, the kinase inhibitor is administered intrathecally or intranasally, such as for direct administration to the brain.

In some aspects, the second therapeutic agent is chemotherapy, radiotherapy, gene therapy, surgery, hormonal therapy, anti-angiogenic therapy or cytokine therapy. In particular aspects, the second therapeutic agent is radiation therapy, chemotherapy, immunotherapy, and/or metabolic modulation. In some aspects, the second therapeutic agent is administered concurrently with the kinase inhibitor. In other aspects, the second therapeutic agent is administered sequentially with the kinase inhibitor.

In a further embodiment, there is provided a method for inhibiting metastasis in a subject comprising administering a kinase inhibitor to a subject identified to have increased activity of at least 2 kinases selected from the group consisting of ADCK4, BTK, CAMK4, CDK5, CDK5R1, CLK3, DAK, FRK, LIMK2, MAP2K7, MAPK12, MAPK7, PAK4, PCTK1, PMVK, PRKACB, PRKACG, PRKCD, PRKCI, SPHK1, TSSK6, UCK2, and ZC3HC1 as compared to a control. In particular aspects, increased activity is the result of increased expression level, post-translational modifications, or sub-cellular localization. In certain aspects, increased activity is measured by an increased expression level. In some aspects, the subject has breast cancer or lung cancer. In particular aspects, the metastasis is further defined as brain metastasis.

In some aspects, the subject is identified to have increased activity of at least 5 kinases (e.g., 6, 7, 8, 9, 10, 11, 12, 13, 14, 15, 16, 17, 18, 19, 20, 21, 22, or 23 kinases) selected from the group consisting of ADCK4, BTK, CAMK4, CDK5, CDK5R1, CLK3, DAK, FRK, LIMK2, MAP2K7, MAPK12, MAPK7, PAK4, PCTK1, PMVK, PRKACB, PRKACG, PRKCD, PRKCI, SPHK1, TSSK6, UCK2, and ZC3HC1 as compared to a control. In certain aspects, the subject is identified to have increased expression of at least 15 kinases selected from the group consisting of ADCK4, BTK, CAMK4, CDK5, CDK5R1, CLK3, DAK, FRK, LIMK2, MAP2K7, MAPK12, MAPK7, PAK4, PCTK1, PMVK, PRKACB, PRKACG, PRKCD, PRKCI, SPHK1, TSSK6, UCK2, and ZC3HC1 as compared to a control. In some aspects, the subject is identified to have increased expression of at least 20 kinases selected from the group consisting of ADCK4, BTK, CAMK4, CDK5, CDK5R1, CLK3, DAK, FRK, LIMK2, MAP2K7, MAPK12, MAPK7, PAK4, PCTK1, PMVK, PRKACB, PRKACG, PRKCD, PRKCI, SPHK1, TSSK6, UCK2, and ZC3HC1 as compared to a control.

In another embodiment, there is provided a composition comprising an effective amount of a kinase inhibitor for the treatment of brain metastasis in a subject having a cancer, wherein the kinase inhibitor targets a kinase selected from the group consisting of ADCK4, BTK, CAMK4, CDK5, CDK5R1, CLK3, LIMK2, PAK4, PMVK, PRKACB, PRKACG, PRKCI, TSSK6, and ZC3HC1.

Further provide herein is a composition comprising an effective amount of a kinase inhibitor and an anti-cancer agent for the treatment of brain metastasis in a subject having a cancer, wherein the kinase inhibitor targets a kinase selected from the group consisting of PCTK1, SPHK1, FRK, MAPK12, ERK5, MAP2K7, UCK2, DAK, and PRKCD.

In certain aspects of the above embodiments, the kinase inhibitor is dinaciclib, bis-indole indirubin, (S)-CR8, kenpaullone, PHA-793887, AT7519, roscovitine, milciclib, SNS-032, olomoucine, BMS-5, Pyr-1, T56-LIMKi, ibrutinib, acalabrutinib, ONO-4059, spebrutinib, BGB-3111, HM71224, DTP3, CDDD_1633, CSDDD_2260, CSDDD_2419, luteolin, ridaura or RXDX-108, SB 203580, doramapimod, LY2228820, indirubin E804, dabrafenib, rebastinib, BML-258, SKI III, SKI 5C, MP A08, SKI 178, PF-543, fingolimod, safingol, fingolimod, safingol, dinaciclib, PHA-793887, AT7519, CYC-065, DCAM-422, CYC-065 or DCAM-422, ERK5-IN-1, BIX 02189, XMD17-109, XMD 8-92, dasatinib, motesanib, doramapimod, pelitinib, sorafenib, vandetanib, canertinib, imatini, PF-3758309, LCH-7749944, glaucarubinone, KY-04031, KY-04045, 1-phenanthryl-tetrahydroisoquinoline derivatives, (–)-β-hydrastine, Inka1, GL-1196, GNE-2861, flavokawain B or alpinetin.

In some aspects of the above embodiments, the cancer is breast cancer. In certain aspects, the breast cancer is further defined as triple negative breast cancer. In some aspects, the cancer is lung cancer. In certain aspects, the subject was not known to have brain metastasis prior to treatment. In other aspects, the subject was known to have one or more brain metastasis prior to treatment. In some aspects, the subject is human.

In certain aspects, the method comprises administering at least a second anti-cancer agent. In some aspects, second anti-cancer agent is chemotherapy, radiotherapy, gene therapy, surgery, hormonal therapy, anti-angiogenic therapy or cytokine therapy. In particular aspects, the second therapeutic agent is radiation therapy, chemotherapy, immunotherapy, or metabolic modulation.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 6A-6B: SPHK1 knockdown significantly delays mortality in MDA-MB-435 model of experimental brain metastasis. (A) Western blot showing shRNA-mediated knockdown efficiency of SPHK1 prior to intracarotid injection. (B) Survival analysis of nude mice injected with $1 \times 10^5$ cells shows that SPHK1 knockdown extends median survival from 57.5 to 77 days.

DESCRIPTION OF ILLUSTRATIVE EMBODIMENTS

Figure 1:
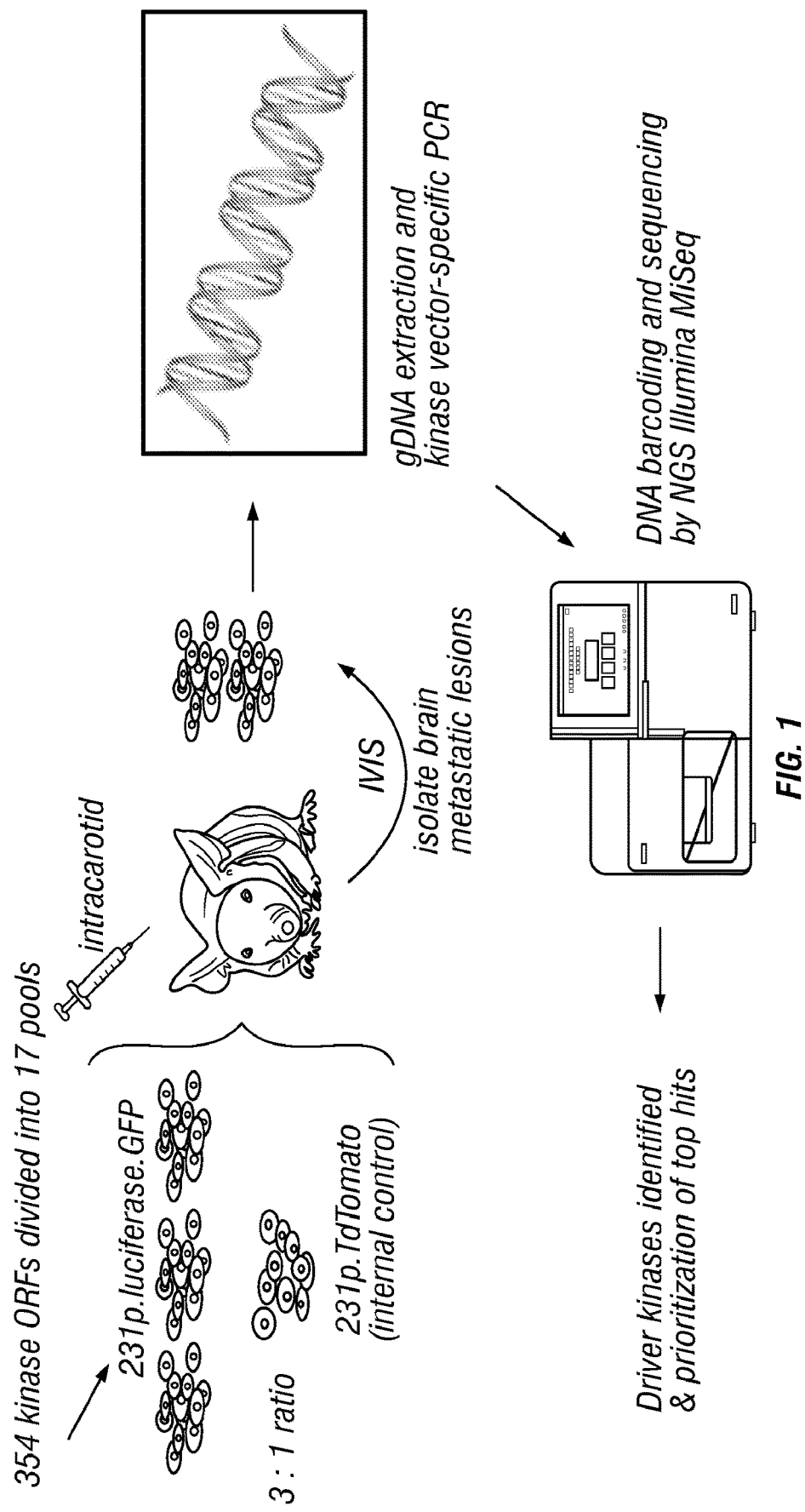
FIG. 1: Schematic of in vivo kinome screen for drivers of brain metastatic growth. MDA-MB-231 parental cells (231p) stably expressing luciferase, GFP, and pools of up to 24 kinases (231p.luciferase.GFP) were mixed with 231p cells expressing TdTomato and an empty pWZL-Neo-Myr-Flag-DEST vector (231p.TdTomato). Cells were mixed at a 3:1 ratio of kinase pool:vector and $2 \times 10^6$ cells were injected into the carotid artery of nude mice. When animals displayed neurological symptoms and their heads were determined to be extremely luciferase-positive by IVIS, mice were sacrificed and brain lesions isolated using a dissecting microscope based on GFP-positivity. Portions of the lesions were subjected to direct RNA extraction, while the remainder was dissociated and the cells cultured in vitro as passage 0. gDNA was extracted from the recovered cells and kinase vector sequences amplified by targeted PCR. This DNA was sequenced by MiSeq, yielding a quantitative readout of in vivo selection.
Figure 2:
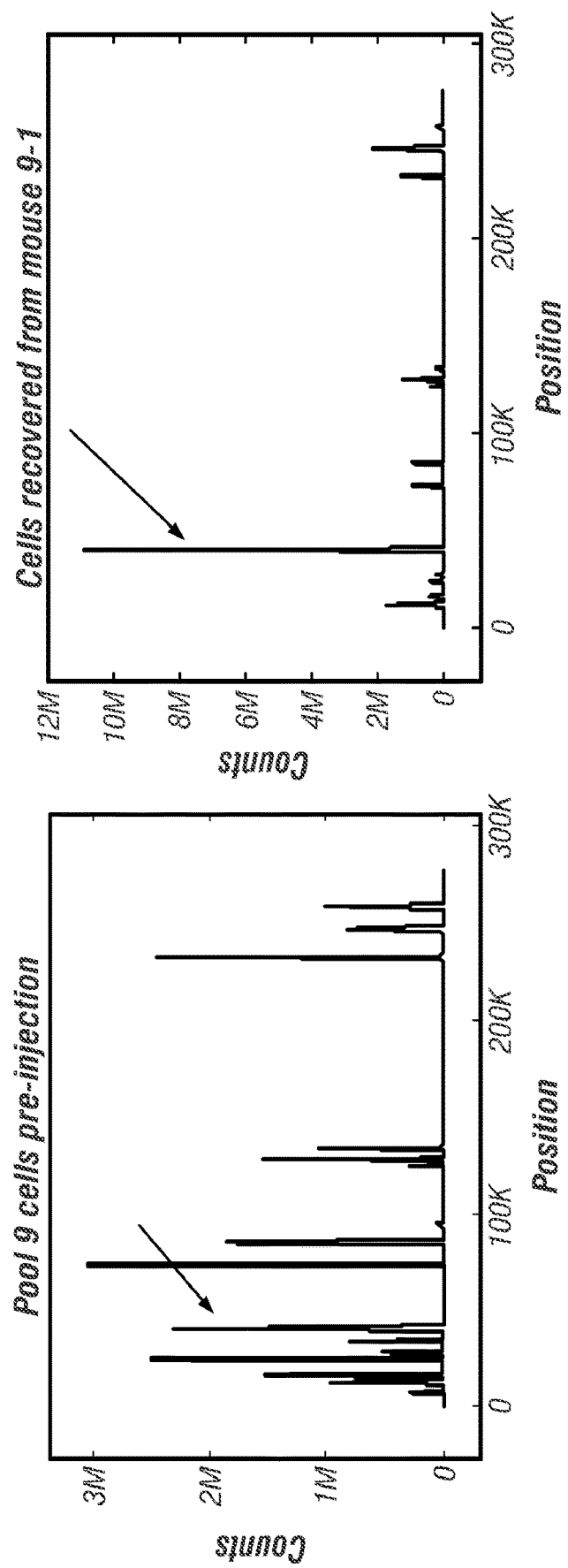
FIG. 2: Example of relative sequence enrichment following in vivo selection. Comparison of kinase sequence read counts prior to and following in vivo selection demonstrates appreciable loss of most sequences in vivo, with notable positive selection of those kinases deemed "hits." Coverage plots were generated with MiSeq Reporter.

To identify driver kinases of brain metastasis for use in the treatment of brain metastasis by taking advantage of the druggability of kinases, the present studies performed an unbiased in vivo screen of the human kinome to uncover novel kinases that promote breast cancer brain metastasis and may serve as therapeutic targets for effective inhibition of brain metastasis. While currently available kinase targets have been identified by their roles in promoting cancer cell growth in a cell culture dish, the presently identified kinases stemmed from a functional in vivo screen specifically looking for drivers of brain metastasis in animals. Therefore, targets identified by this method play roles specifically in the growth of brain metastasis.

Specifically, a 354-kinase library was divided into 17 pools of 21 kinases each in the MDA-MB-231 human triple negative breast cancer cell line and the resulting cells were injected into the carotid artery of nude mice to induce experimental brain metastasis. Several pools of these kinases led to dramatically increased brain metastasis-specific mortality compared to 231 vector control cells. Next-generation sequencing (NGS) and genetic analyses identified that these aggressive brain metastases were enriched with certain kinases in vivo. These efforts revealed more than 20 brain metastasis-promoting kinases including ADCK4 (COQ8B), BTK, CAMK4, CDK5, CDK5R1, CLK3, DAK, FRK, LIMK2, MAP2K7, MAPK12 (p38γ), MAPK7 (ERK5), PAK4, PCTK1, PMVK, PRKACB, PRKACG, PRKCD, PRKCI, SPHK1, TSSK6, UCK2, and ZC3HC1 (Table 1).

To further test these kinases, some of the kinases were genetically knocked down to test the effect of targeting these identified brain metastasis driver kinases for inhibition of brain metastases. Indeed, knocking down some of the top hits inhibited experimental brain metastasis and significantly prolonged survival of mice bearing brain metastasis. Specifically, knockdown of kinases, such as PCTK1, SPHK1, MAPK12, and CDK5, led to a decrease in cell proliferation and delayed brain metastasis growth in human cancer cell models and in early stages of a 4T1 mouse mammary tumor model of experimental brain metastasis.

The efficacy of targeting some of these kinases identified in the screen to inhibit brain metastasis was also assayed in the present studies by overexpression of the kinase in an experimental brain metastasis mouse model. Overexpression of CDK5, PCTK1, MAPK12, LIMK2, and SPHK1 resulted in increased brain metastasis growth. In particular, overexpression of the kinases, such as SPHK1, PCTK1, LIMK2 and CDK5, resulted in shortened survival in an experimental brain metastasis mouse model. Thus, the kinases identified in the screen herein may be targeted for the inhibition of brain metastasis, such as breast cancer brain metastasis.

Accordingly, in certain embodiments, the present disclosure provides methods of targeting the brain metastasis-driving kinases identified from the kinome screen for effective inhibition of brain metastasis. The kinases identified herein may be targeted by inhibitors including genetic, chemical, immunologic, and metabolic inhibitors. The kinase inhibitors may be used in combination with current standard of care for brain metastasis, e.g., radiation therapy, chemotherapy, immunotherapy, and metabolic modulation.

I. Definitions

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

An "inhibitor" or "antagonist" is a compound that lowers or inhibits the activity of a given target, such as a kinase.

As used herein, the terms "protein kinase" or "kinase" are used in accordance with its plain ordinary meaning and refers to an enzyme that is capable of catalyzing the transfer of a phosphate group from high-energy, phosphate-donating molecules to specific substrates, such as phosphorylating an amino acid residue, e.g., an amino acid residue on a protein, or amino alcohol. Typically specific serine, threonine, or tyrosine residues are phosphorylated. Thus, protein kinase encompasses serine protein kinases, threonine protein kinases, and tyrosine protein kinases. An "inhibitor of a protein kinase" or "kinase inhibitor" is a compound or agent that reduces the activity of a protein kinase. In some embodiments, a "kinase inhibitor" is a compound that reduces the activity of the protein kinase by binding to the protein kinase. Thus, a "kinase inhibitor" can inhibit activity of the enzyme in a competitive, or a noncompetitive manner.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, the resulting reaction product can be produced directly from a reaction between the added reagents or from an intermediate from one or more of the added reagents which can be produced in the reaction mixture. The term "contacting" includes incubating an inhibitor with the kinase.

As defined herein, the term "inhibition", "inhibit", "inhibiting" and the like in reference to a kinase-inhibitor interaction means negatively affecting (e.g., decreasing) the activity of the kinase relative to the activity of the kinase in the absence of the inhibitor. Thus, inhibition includes, at least in part, partially or totally blocking stimulation, decreasing, preventing, or delaying activation, or inactivating, desensitizing, or down-regulating signal transduction. Similarly an "inhibitor" is a compound that inhibits kinase activity, e.g., by binding, partially or totally block stimulation, decrease, prevent, or delay activation, or inactivate, desensitize, or down-regulate signal transduction.

By "selective" it is meant that the affinity for a given kinase is at least 5-fold to 10-fold, preferably 25-fold, more preferred 100-fold, still preferred 150-fold higher than the affinity for other kinases.

As used herein, the phrase "ATP-binding pocket" refers to the active site of a kinase that binds ATP. The active site of the kinase where ATP binds is the set of amino acid residues that are able to interact with and or bind to an ATP molecule or an ATP competitive inhibitor.

As used herein, the term "mutated" refers to a kinase with a non-natural (e.g. non-wild type) amino acid sequence. A mutated kinase is typically recombinant (e.g. engineered). In some embodiments as described below, the mutated kinase has a cysteine residue substitution at the gatekeeper amino acid position. As used herein, the term "unmutated" refers to the corresponding kinase wherein the mutation (e.g., a cysteine residue is substituted for a gatekeeper amino acid position) is not present (e.g., the natural or wild-type sequence). Thus, in some instances, unmutated refers to the wild-type or natural kinase. In some other instances, the corresponding kinase is another recombinant kinase having similar but distinct substitutions.

A "metastasis" is a region of cancer cells, distinct from the primary tumor location resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms. A "detectable" metastasis is a cluster of cells that may be identifiable by magnetic resonance imaging, computerized tomography or positron emission tomography. In certain non-limiting embodiments, a cluster of metastatic cells may include at least about $1 \times 10^7$ cells. In certain embodiments, a detectable metastasis can include a cluster of cells having a size greater than about 5 mm or about 10 mm.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al., 1998), and natural product extract libraries. In another embodiment, the compounds are small, organic non-peptidic compounds. In a further embodiment, a small molecule is not biosynthetic.

II. Target Kinases

In certain embodiments, the present disclosure provides methods of treating (e.g., inhibiting or decreasing) metastasis, such as brain metastasis, by administering an inhibitor of a kinase identified as a metastasis promoting kinase (Table 1) by the in vivo kinase screen of the present studies. The treatment may be in a subject with a primary tumor in order to inhibit development of metastasis, particularly brain metastasis. In other aspects, the subject may be diagnosed with a metastatic tumor, such as brain metastasis, and the treatment decreases brain metastasis, such as by at least 10%, particularly 20%, 30%, 40%, 50%, 60%, 70%, 80%, 90%, 95%, 98%, 99%, or 100%.

Therapeutic agents, such as kinase inhibitors, which can reduce the level of the metastasis-promoting kinase includes those generally known in the art, such as antisense nucleic acids, shRNA, siRNA, a small molecule, a polypeptide, an antibody or a fragment of an antibody, a polynucleotide, a carbohydrate including a polysaccharide, a lipid, a drug, as well as mimics, derivatives, and combinations thereof. In particular aspects, the kinases are inhibited by kinase inhibitors selective for the specific kinase. Exemplary selective kinase inhibitors for each kinase in Table 1 are disclosed herein; however, any selective kinase inhibitor known in the art may be used for the present methods.

TABLE 1

Kinase sequences enriched in vivo as determined by NGS sequencing.

| Official Symbol | Gene Description |
|---|---|
| ADCK4 | aarF domain containing kinase 4 |
| BTK | Bruton agammaglobulinemia tyrosine kinase |
| CAMK4 | calcium/calmodulin dependent protein kinase IV |
| CDK5 | cyclin-dependent kinase 5 |
| CDK5R1 | cyclin-dependent kinase 5, regulatory subunit 1 (p35) |
| CLK3 | CDC-like kinase 3 |
| DAK | dihydroxyacetone kinase 2 homolog |
| FRK | fyn-related kinase |
| LIMK2 | LIM domain kinase 2 |
| MAP2K7 | mitogen-activated protein kinase kinase 7 |
| MAPK12 | mitogen-activated protein kinase 12 |
| MAPK7 | mitogen-activated protein kinase 7, transcript variant 2 |
| MARK4 | MAP/microtubule affinity-regulating kinase 4 |
| PAK4 | p21(CDKN1A)-activated kinase 4 |
| PCTK1 | PCTAIRE protein kinase 1, transcript variant 2 |
| PMVK | phosphomevalonate kinase |
| PRKACB | protein kinase, cAMP-dependent, catalytic, beta |
| PRKACG | protein kinase, cAMP-dependent, catalytic, gamma |
| PRKCD | protein kinase C, delta |
| PRKCI | protein kinase C, iota |
| SPHK1 | sphingosine kinase 1 |
| TSSK6 | testis-specific serine kinase 6 |
| UCK2 | uridine-cytidine kinase 2 |
| ZC3HC1 | zinc finger, C3HC-type containing 1 |

A. PCTK1 (CDK16)

The serine/threonine-protein kinase PCTAIRE-1 (PCTK1) gene, also referred to as cyclin dependent kinase 16 (CDK16), encodes a kinase that plays a role in vesicle-mediated transport processes and exocytosis. It also regulates neuron differentiation and dendrite development. PCTK1 may be inhibited by RNAi and/or a pharmacological inhibitor selective for PCTK1. For example, one inhibitor selective for PCTK1 which may be used in the present methods is indirubin E804 or an analog thereof (Hoessel et al., 1999; Cweik et al., 2015; both incorporated herein by reference). The inhibitor binds to the ATP site by interacting with the hinge region via H-bond interactions. Other inhibitors that may be used to inhibit PCTK1 include type I kinase inhibitors, such as triazolo-diamine compound Cdk1/2 Inhibitor III, Alsterpaullone, 2-Cyanoethyl, Indirubin E804 and the aminopyrimidinyl compound Cdk2/9 Inhibitor. CDK2 inhibitors, such as oxindoles GW300657X and GW416981X, as well as the pyrazolo[1,5-b]pyridazine compound GW779439X, may also be used for the inhibition of PCTK1.

In particular aspects, dabrafenib or rebastinib is used for the inhibition of PCTK1. Rebastinib is a multi-targeted type II kinase inhibitor that was developed to inhibit BCR-ABL as well as the drug-resistant gatekeeper mutant ABL. Dabrafenib is an ATP-competitive type I inhibitor of mutant $BRAF^{V600E}$ that has been approved for clinical use in advanced melanoma. In one specific aspects, the inhibitor of PCTK1 is rebastinib.

The indirubin E804 may be synthesized by the following method. Briefly, to a solution of indoxyl acetate 2 (5.00 g, 28.5 mmol) in anhydrous methanol (70 mL) under nitrogen is added isatin 1 (4.20 g, 28.8 mmol) and sodium carbonate (6.50 g, 61.3 mmol). After 30 min of stirring and standing for 24 h, slurry is filtered and washed with cold methanol and cold water. Obtained indirubin 3 (2.50 g, 9.5 mmol) and hydroxylamine hydrochloride (1.7 g, 24.7 mmol) are refluxed together in pyridine (60 mL) for 1.5 h. Subsequently, mixture is poured into a 1M solution of hydrochloric acid (100 mL). The red/orange precipitate is filtered off, re-dissolved in 1M sodium hydroxide (70 mL) and re-precipitated with 1M hydrochloric acid (150 mL). The crude product is filtered, dried and recrystallized from ethanol/water (7:2) to give the product as bright red/orange crystals. In the end, Indirubin-3'-oximine 4 (55.4 mg, 0.20 mmol) and 4-bromobutane-1,2-diol 5 (40.1 mg, 0.24 mmol) are dissolved in anhydrous dimethylformamide (1.5 mL). To this was added triethylamine (33 µL, 0.24 mmol). The reaction is stirred under nitrogen for 4 h before the solvent is removed in vacuo to produce a crude brown oil which was purified via column chromatography to give the product as a red solid (36 mg, 41% yield).

B. SPHK1

Sphingosine kinase (SPHK1) promotes cell growth and survival and is a key enzyme that regulates the S1P/ceramide rheostat. Non-isozyme specific inhibitors of SPHKs, such as L-threo-dihydrosphingosine (safingol) and N,N-dimethylsphingosine (DMS) may be used in the present methods. In some aspects, SPHK1 is inhibited by BML-258 as described in U.S. Pat. No. 8,372,888, 3-(4-chloro-phenyl)-adamantane-1-carboxylic acid (pyridin-4-ylmethyl)-amide as described in U.S. Patent Publication No. 20080167352, [(2R)-1-[[4-[[3-(benzenesulfonyl methyl)-5-methylphenoxy] methyl] phenyl] methyl] pyrrolidin-2-yl] methanol (PF-543), Sphingosine Kinase Inhibitor 2 (SKI II; 4-[[4-(4-Chlorophenyl)-2-thiazolyl]amino]phenol), SKI 5C (CAY10621), N,N-Dimethylsphingosine ((2S,3R,4E)-2-(Dimethylamino)-4-octadecene-1,3-diol), MP A08 (4-Methyl-N-[2-[[[2-[[(4-methylphenyl)sulfonyl]amino] phenyl]imino]methyl]phenyl]benzenesulfonamide), SKI 178 (N'-(1-(3,4-Dimethoxyphenyl)ethylidene)-3-(4-methoxyphenyl)-1H-pyrazole-5-carbohydrazide), or an analog, derivative or pharmaceutically acceptable salt thereof. In particular aspects, the inhibitor of SPHK1 is fingolimod (Gilenya) or safingol.

C. MAPK12 (p38γ)

Mitogen-activated protein kinase 12 (MAP kinase 12), also known as extracellular signal-regulated kinase 6 (ERK6) or stress-activated protein kinase 3 (SAPK3), is an enzyme that in humans is encoded by the MAPK12 gene. Activation of members of the mitogen-activated protein kinase family is a major mechanism for transduction of extracellular signals. Stress-activated protein kinases are one subclass of MAP kinases. The protein encoded by this gene functions as a signal transducer during differentiation of myoblasts to myotubes. MAPK12 may be inhibited by SB 203580, doramapimod (BIRB 796), LY2228820, or other inhibitors of MAPK12 known in the art.

D. CDK5 and CDK5R1

Cell division protein kinase 5 is an enzyme that in humans is encoded by the CDK5 gene. CDK5 is required for proper development of the brain and to be activated, CDK5 must associate with CDK5R1 or CDK5R2. CDK5 or CDK5R1 may be inhibited in the present methods by dinaciclib (SCH727965), bis-indole indirubin, (S)-CR8, kenpaullone, PHA-793887, AT7519, roscovitine (seliciclib, CYC202), milciclib (PHA-848125), SNS-032 (BMS-387032), or olomoucine. In particular aspects, the inhibitor of CDK5 is CYC-065 or DCAM-422.

E. LIMK2

LIM kinase 2 (LIMK2) is a regulator of the actin cytoskeleton. LIMK2 phosphorylates and thus inactivates cofilin, a member of the actin depolymerizing factor (ADF) family. Exemplary inhibitors of LIMK2 include, but are not limited to, BMS-5 (CAS No. 1338247-35-0), Pyr-1 (LIMNIB), damnacanthal, Par-3, T56-LIMKi, and LX7101. LX7101 is a pyrrolopyrimidine-based, topically-delivered inhibitor of LIM domain kinase 2 (LIMK2), a kinase associated with the regulation of intraocular pressure.

F. ADCK4 (COQ8B)

Coenzyme Q8B (COQ8B) or AarF Domain-Containing Protein Kinase 4 (ADCK4) is a lipid-soluble electron transporter for aerobic cellular respiration. ADCK4 may be inhibited by RNAi or inhibitors known in the art.

G. BTK

Bruton's tyrosine kinase (Btk or BTK) also known as tyrosine-protein kinase BTK is an enzyme that in humans is encoded by the BTK gene. BTK is a kinase that plays a role in B-cell development. The function of BTK in signaling pathways activated by the engagement of the B cell receptor (BCR) and FCER1 on mast cells is well established. Functional mutations in BTK in humans result in a primary immunodeficiency disease characterized by a defect in B cell development with a block between pro- and pre-B cell stages. Exemplary inhibitors of BTK include, but are not limited to, ibrutinib (PCI-32765), acalabrutinib, ONO-4059, spebrutinib (AVL-292, CC-292), BGB-3111, and HM71224.

H. CAMK4

Calcium/calmodulin-dependent protein kinase type IV is an enzyme that in humans is encoded by the CAMK4 gene. The product of this gene belongs to the serine/threonine protein kinase family, and to the Ca2+/calmodulin-dependent protein kinase subfamily. This enzyme is a multifunctional serine/threonine protein kinase with limited tissue distribution that has been implicated in transcriptional regulation in lymphocytes, neurons and male germ cells. An exemplary inhibitor of CAMK4 is KN-93 (N-[2-[[[3-(4-Chlorophenyl)-2-propenyl]methylamino]methyl]phenyl]-N-(2-hydroxyethyl)-4-methoxybenzenesulphonamide).

I. CLK3

CDC Like Kinase 3 (CLK3) is a nuclear dual-specificity kinase that regulates the intranuclear distribution of the serine/arginine-rich (SR) family of splicing factors. An exemplary inhibitor of CLK3 is KH-CB 19. Other inhibitors that may be used include R547, A-674563, NVP-TAE684, and AT-7519.

J. DAK

Triokinase/FMN cyclase or Dihydroxyacetone Kinase 2 Homolog (DAK) is an enzyme that in humans is encoded by the DAK gene. DAK phosphorylates dihydroxyacetone, and also catalyzes the formation of riboflavin 4',5'-phosphate (aka cyclin FMN) from FAD. DAK may be inhibited by RNAi or inhibitors known in the art.

K. ERK5 (MAPK7)

Mitogen-activated protein kinase 7 also known as MAP kinase 7 and ERK5 is a member of the MAP kinase family. MAP kinases act as an integration point for multiple biochemical signals, and are involved in a wide variety of cellular processes such as proliferation, differentiation, transcription regulation and development. This kinase is specifically activated by mitogen-activated protein kinase kinase 5 (MAP2K5/MEK5). It is involved in the downstream signaling processes of various receptor molecules including receptor tyrosine kinases, and G protein-coupled receptors. In response to extracellular signals, this kinase translocates to the cell nucleus, where it regulates gene expression by phosphorylating, and activating different transcription factors. An exemplary inhibitors of ERK5 include, but are not limited to, ERK5-IN-1 (11-Cyclopentyl-2-[[2-ethoxy-4-[[4-(4-methyl-1-piperazinyl)-1-piperidinyl]carbonyl]phenyl]amino]-5,11-dihydro-5-methyl-6H-pyrimido[4,5-b][1,4]benzodiazepin-6-one), BIX 02189, XMD17-109, and XMD 8-92.

L. FRK (PTK5)

Fyn-related kinase (FRK) belongs to the TYR family of protein kinases. This tyrosine kinase is a nuclear protein and may function during G1 and S phase of the cell cycle and suppress growth. Exemplary inhibitors of FRK include, but are not limited to, tyrosine kinase inhibitors such as dasatinib, motesanib (A1VIG-706), doramapimod (BIRB 796), pelitinib (EKB-569), sorafenib, vandetanib, canertinib (CI-1033) and imatinib (STI-571).

M. MAP2K7 (MKK7/GADD45b)

Dual specificity mitogen-activated protein kinase kinase 7, also known as MAP kinase kinase 7 or MKK7, is an enzyme that in humans is encoded by the MAP2K7 gene. This protein is a member of the mitogen-activated protein kinase kinase family. MKK7 is involved in signal transduction mediating the cell responses to proinflammatory cytokines, and environmental stresses. MAP2K7 may be inhibited by DTP3 ((R)-2-((R)-2-acetamido-3-(4-hydroxyphenyl)propanamido)-N—((R)-1-amino-1-oxo-3-phenylpropan-2-yl)-5-guanidinopentanamide trifluoroacetate).

N. PAK4

Serine/threonine-protein kinase PAK 4 is one of six members of the PAK family of serine/threonine kinases. PAK4 localizes in sub-cellular domains of the cytoplasm and nucleus. PAK4 regulates cytoskeleton remodeling, phenotypic signaling and gene expression, and affects directional motility, invasion, metastasis, and growth. PAK4 may be inhibited by PF-3758309, LCH-7749944, glaucarubinone, KY-04031, KY-04045, 1-phenanthryl-tetrahydroisoquinoline derivatives, (−)-β-hydrastine, Inka1, GL-1196, GNE-2861, and microRNAs such as miR-145, miR-433, and miR-126.

O. PMVK

Phosphomevalonate kinase (PMVK) is in the mevalonate pathway and it catalyzes the conversion of mevalonate 5-phosphate to mevalonate 5-diphosphate, which is the fifth step in the mevalonate pathway of isoprenoid biosynthesis. PMVK may be inhibited by administration of CSDDD_1633 (1,4-bis((2-(($\gamma^1$-oxidaneyl)dioxo-$\gamma^6$-sulfaneyl)-4-methylphenyl)amino)-5,8-dihydroxy-4a,9a-dihydroanthracene-9,10-dione), CSDDD_2260 (2,2'-((4-((2-($\gamma^1$-oxidaneyl)-2-oxoethyl)thio)-[1,1'-biphenyl]-2,6-diyl)bis(sulfanediyl))diacetate, CSDDD_2419 ((E)-4-((2,4-dihydroxyphenyl)diazenyl)-5-methylnaphthalene-2,7-disulfonate) or luteolin as described in Boonsri et al., 2013; incorporated herein by reference.

P. PRKACB and PRKACG cAMP-dependent protein kinase catalytic subunit beta (PRKACB) is a signaling molecule for a variety of cellular functions. cAMP exerts its effects by activating the protein kinase A (PKA), which transduces the signal through phosphorylation of different target proteins. The inactive holoenzyme of PKA is a tetramer composed of two regulatory and two catalytic subunits. cAMP causes the dissociation of the inactive holoenzyme into a dimer of regulatory subunits bound to four cAMP and two free monomeric catalytic subunits. AMP-dependent protein kinase catalytic subunit gamma (PRKACG) plays roles in the CCR5 pathway in macrophages and signaling in gap junctions. PRKACB or PRKACG may be inhibited by RNAi or inhibitors known in the art.

Q. PRKCI and PRKCD

Protein kinase C iota type (PRKCI) and Protein kinase C delta type (PRKCD) are members of the protein kinase C (PKC) family of serine/threonine protein kinases. The PKC family comprises at least eight members, which are differentially expressed and are involved in a wide variety of cellular processes. This protein kinase is calcium-independent and phospholipid-dependent. It is not activated by phorbolesters or diacylglycerol. This kinase can be recruited to vesicle tubular clusters (VTCs) by direct interaction with the small GTPase RAB2, where this kinase phosphorylates glyceraldehyde-3-phosphate dehydrogenase (GAPD/GAPDH) and plays a role in microtubule dynamics in the early secretory pathway. This kinase is found to be necessary for BCL-ABL-mediated resistance to drug-induced apoptosis and therefore protects leukemia cells against drug-induced apoptosis. Exemplary inhibitors for these kinases include, but are not limited to, protein kinase inhibitors such as Bisindolylmaleimide II, Calphostin C, Dihydrosphingosine, and LY 333531 hydrochloride. In specific aspects, the inhibitor of PRKCI is ridaura (auranofin) or RXDX-108.

R. TSSK6

Testis-specific serine kinase 6 (TSSK6) The encoded kinase has a broad expression pattern but is described as testis-specific due to effects on fertility. TSSK6 may be inhibited by RNAi or inhibitors known in the art.

S. UCK2

Uridine-cytidine kinase 2 (UCK2) catalyzes the phosphorylation of uridine and cytidine to uridine monophosphate (UMP) and cytidine monophosphate (CMP), respectively. This is the first step in the production of the pyrimidine nucleoside triphosphates required for RNA and DNA synthesis. In some aspects, the inhibitor of UCK2 is flavokawain B or alpinetin (Malami et al., 2016).

T. ZC3HC1

Nuclear-interacting partner of ALK (NIPA), also known as zinc finger C3HC-type protein 1 (ZC3HC1) is ubiquitously expressed in many tissues and cell types though exclusively expressed in the nuclear subcellular location. NIPA is a skp1 cullin F-box (SCF)-type ubiquitin E3 ligase (SCFNIPA) complex protein involved in regulating entry into mitosis. ZC3HC1 may be inhibited by RNAi or inhibitors known in the art.

U. RNA Interference

In some embodiments, a kinase may be inhibited by RNA interference, such as siRNA or miRNA. The RNA may be siRNA, shRNA, plasmid, mRNA, miRNA, or ncRNA, particularly siRNA or miRNA therapeutics. The miRNA may be a miRNA mimic, or a miRNA precursor. The size of the RNA may be less than 100 nucleotides in length, such as less than 75 nucleotides, particularly less than 50 nucleotides in length. For example, the RNA may have a length of about 10-100 nucleotides, such as 20-50 nucleotides, particularly 10-20, 15-25, 20-30, 25-35, 30-40, or 45-50 nucleotides.

The RNA may be modified or non-modified. The RNA may comprise an alteration of one or more nucleotides. Such alterations can include the addition of non-nucleotide material, such as to the end(s) of the RNA or internally (at one or more nucleotides of the RNA). In certain aspects, the RNA molecule contains a 3'-hydroxyl group. Nucleotides in the RNA molecules of the present disclosure can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Publication No. 20040019001 and U.S. Pat. No. 6,673,611 (each of which is incorporated by reference in its entirety). Collectively, all such altered nucleic acids or RNAs described above are referred to as modified siRNAs.

Preferably, RNAi is capable of decreasing the expression of a protein by at least 10%, 20%, 30%, or 40%, more preferably by at least 50%, 60%, or 70%, and even more preferably by at least 75%, 80%, 90%, 95% or more.

The siRNA as used in the methods or compositions described herein may comprise a portion which is complementary to an mRNA sequence encoded by NCBI Reference Sequence for the stated kinase. In an embodiment, the siRNA comprises a double-stranded portion (duplex). In an embodiment, the siRNA is 20-25 nucleotides in length. In an embodiment the siRNA comprises a 19-21 core RNA duplex with a one or 2 nucleotide 3' overhang on, independently, either one or both strands. In an embodiment, the overhang is UU. The siRNA can be 5' phosphorylated or not and may be modified with any of the known modifications in the art to improve efficacy and/or resistance to nuclease degradation. In a non-limiting embodiment, the siRNA can be administered such that it is transfected into one or more cells. In one embodiment, a siRNA may comprise a double-stranded RNA comprising a first and second strand, wherein one strand of the RNA is 80, 85, 90, 95 or 100% complementary to a portion of an RNA transcript of a gene.

In one embodiment, a single strand component of a siRNA of the present disclosure is from 14 to 50 nucleotides in length. In another embodiment, a single strand component of a siRNA is 14, 15, 16, 17, 18, 19, 20, 21, 22, 23, 24, 25, 26, 27, or 28 nucleotides in length. In yet another embodiment, a single strand component of a siRNA of the present disclosure is 21 nucleotides in length. In yet another embodiment, a single strand component of a siRNA of the present disclosure is 22 nucleotides in length. In yet another embodiment, a single strand component of a siRNA of the present disclosure is 23 nucleotides in length. In one embodiment, a siRNA of the present disclosure is from 28 to 56 nucleotides in length.

III. Methods of Treatment

Provided herein are methods for treating or delaying progression of cancer, particularly cancer metastasis, in an individual comprising administering to the individual an effective amount of a kinase inhibitor, such as an inhibitor for the metastasis-promoting kinase identified in the present disclosure (Table 1). Certain embodiments of the present disclosure concern methods of treating or preventing disease in a subject involving administration of an inhibitor of a metastasis-promoting kinase. The disease may be any disease that can affect a subject. In particular embodiments, the disease is a hyperproliferative disease. In more particular embodiments, the disease is cancer.

In some embodiments, there is provided a method for inhibiting growth and/or survival of metastatic cancer cells in the brain of a subject, comprising treating the subject with a therapeutically effective amount of an inhibitor of a kinase of Table 1. In certain embodiments, there is provided a method of determining whether a brain tumor or metastatic brain tumor in a subject will receive therapeutic benefit from treatment with an inhibitor of a kinase of Table 1, such as by measuring the expression of said kinase in the subject, such as in the blood of said subject.

The cancer may be a solid tumor, metastatic cancer, or non-metastatic cancer. In certain embodiments, the cancer may originate in the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In certain embodiments, the cancer is human ovarian cancer or breast cancer. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Nonetheless, it is also recognized that the present disclosure may also be used to treat a non-cancerous disease (e.g., a fungal infection, a bacterial infection, a viral infection, and/or a neurodegenerative disease).

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The kinase inhibitors for the present methods can reduce the level of an overexpressed kinase include those generally known in the art, such as antibodies, antisense, shRNA, siRNA, or small molecule inhibitors. Administration may be by injection, for example, intravenous, intrathecal, intramuscular or subcutaneously, intranasal, and oral. In many cases, and particularly in the case of already detected brain metastases the use of a therapeutic composition which either passes through the blood brain barrier or administration that avoids this requirement (for example intrathecal or intranasal) is desirable. Combinations of treatment that provide both systemic and brain availability of the therapeutic may also be used.

Therapeutically effective amounts of the therapeutic agent(s) can be administered by a number of routes, including parenteral administration, for example, intravenous, intraperitoneal, intramuscular, intrasternal, or intraarticular injection, or infusion. In particular aspects, the therapeutic agents(s) are administered directly to the site of metastasis, such as the brain or by methods that pass the blood brain barrier, such as intrathecally or intranasally. In some aspects, the therapeutic agent(s) are administered both systemically and directly to the site of metastasis, such as the brain.

The therapeutically effective amount of the kinase inhibitor is that amount that achieves a desired effect in a subject being treated. For instance, this can be the amount of kinase inhibitor necessary to inhibit advancement, or to cause regression of cancer, or which is capable of relieving symptoms caused by a cancer.

The kinase inhibitor(s) can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of kinase inhibitor(s) will be dependent on the subject being treated, the severity and type of the affliction, and the manner of administration. The exact amount of kinase inhibitor(s) is readily determined by one of skill in the art based on the age, weight, sex, and physiological condition of the subject. Effective doses can be extrapolated from dose-response curves derived from in vitro or animal model test systems.

A. Pharmaceutical Compositions

Certain of the methods set forth herein pertain to methods involving the administration of a pharmaceutically effective amount of a composition comprising inhibitor(s) of metastasis-promoting kinases identified in the present disclosure. The use of media and agents for pharmaceutical active substances is well known in the art. Except insofar as any conventional media or agent is incompatible with the active ingredient, its use in the therapeutic compositions is contemplated. Supplementary active ingredients can also be incorporated into the compositions, and these are discussed in greater detail below. For human administration, preparations preferably meet sterility, pyrogenicity, general safety and purity standards as required by FDA Office of Biologics standards.

The present disclosure contemplates methods using compositions that are sterile solutions for injection or for application by any other route as discussed in greater detail below. A person of ordinary skill in the art would be familiar with techniques for generating sterile solutions for injection or application by any other route. Sterile injectable solutions are prepared by incorporating the active compounds in the required amount in the appropriate solvent with various of the other ingredients familiar to a person of skill in the art.

The formulation of the composition may vary depending upon the route of administration. For parenteral administration in an aqueous solution, for example, the solution should be suitably buffered and the liquid diluent first rendered isotonic with sufficient saline or glucose. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, formulations for administration via an implantable drug delivery device, and any other form. One may also use nasal solutions or sprays, aerosols or inhalants in the present disclosure.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. A person of ordinary skill in the art would be familiar with well-known techniques for preparation of oral formulations.

In certain embodiments, pharmaceutical composition includes at least about 0.1% by weight of the active agent. The composition may include, for example, about 0.01%. In other embodiments, the pharmaceutical composition includes about 2% to about 75% of the weight of the composition, or between about 25% to about 60% by weight of the composition, for example, and any range derivable therein.

The pharmaceutical composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. The composition may be stable under the conditions of manufacture and storage, and preserved against the contaminating action of microorganisms, such as bacteria and fungi. It will be appreciated that exotoxin contamination should be kept minimally at a safe level, for example, less than 0.5 ng/mg protein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. In many cases, it will be preferable to include isotonic agents, such as, for example, sugars, sodium chloride or combinations thereof.

In other embodiments, one may use nasal solutions or sprays, aerosols or inhalants in the present disclosure. Nasal solutions may be aqueous solutions designed to be administered to the nasal passages in drops or sprays.

Sterile injectable solutions are prepared by incorporating the nanoparticles in the required amount in the appropriate solvent with various of the other ingredients enumerated above, as required, followed by sterilization.

2. Routes of Administration

Upon formulation, kinase inhibitor(s) will be administered in a manner compatible with the dosage formulation and in such amount as is therapeutically effective.

The kinase inhibitor(s) can be administered to the subject using any method known to those of ordinary skill in the art. For example, a pharmaceutically effective amount of a composition comprising nanoparticles may be administered intravenously, intracerebrally, intracranially, intrathecally, into the substantia nigra or the region of the substantia nigra, intradermally, intraarterially, intraperitoneally, intralesionally, intratracheally, intranasally, topically, intramuscularly, intraperitoneally, subcutaneously, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990). In particular embodiments, the composition is administered to a subject using a drug delivery device.

3. Dosage

A pharmaceutically effective amount of the kinase inhibitor(s) is determined based on the intended goal, for example inhibition of cell death. The quantity to be administered, both according to number of treatments and dose, depends on the subject to be treated, the state of the subject, the protection desired, and the route of administration. Precise amounts of the therapeutic agent also depend on the judgment of the practitioner and are peculiar to each individual.

For example, a dose of the therapeutic agent may be about 0.0001 milligrams to about 1.0 milligrams, or about 0.001 milligrams to about 0.1 milligrams, or about 0.1 milligrams to about 1.0 milligrams, or even about 10 milligrams per dose or so. Multiple doses can also be administered. In some embodiments, a dose is at least about 0.0001 milligrams. In further embodiments, a dose is at least about 0.001 milligrams. In still further embodiments, a dose is at least 0.01 milligrams. In still further embodiments, a dose is at least about 0.1 milligrams. In more particular embodiments, a dose may be at least 1.0 milligrams. In even more particular embodiments, a dose may be at least 10 milligrams. In further embodiments, a dose is at least 100 milligrams or higher.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The dose can be repeated as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, the method may provide a continuous supply of a pharmaceutical composition to the patient. This could be accomplished by catheterization, followed by continuous administration of the therapeutic agent. The administration could be intra-operative or post-operative.

B. Combination Treatments

Certain embodiments of the present disclosure provide for the administration or application of one or more secondary forms of therapies for the treatment or prevention of a disease. For example, the disease may be a hyperproliferative disease, such as cancer.

The secondary form of therapy may be administration of one or more secondary pharmacological agents that can be applied in the treatment or prevention of cancer. If the secondary therapy is a pharmacological agent, it may be administered prior to, concurrently, or following administration of the kinase inhibitor(s).

The interval between the administration of the kinase inhibitor(s) and the secondary therapy may be any interval as determined by those of ordinary skill in the art. For example, the interval may be minutes to weeks. In embodiments where the agents are separately administered, one would generally ensure that a long period of time did not expire between the time of each delivery, such that each therapeutic agent would still be able to exert an advantageously combined effect on the subject. For example, the interval between therapeutic agents may be about 12 h to about 24 h of each other and, more preferably, within about 6 hours to about 12 h of each other. In some situations the time period for treatment may be extended, however, where several days (2, 3, 4, 5, 6 or 7) to several weeks (1, 2, 3, 4, 5, 6, 7 or 8) lapse between the respective administrations. In some embodiments, the timing of administration of a secondary therapeutic agent is determined based on the response of the subject to the nanoparticles.

Various combinations may be employed. For the example below a kinase inhibitor composition is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present disclosure to a patient will follow general protocols for the administration of such compounds, taking into account the toxicity, if any, of the agents. Therefore, in some embodiments there is a step of monitoring toxicity that is attributable to combination therapy. It is expected that the treatment cycles may be repeated. It also is contemplated that various standard therapies, as well as surgical intervention, may be applied in combination with the described therapy.

In specific aspects, it is contemplated that a standard therapy will include chemotherapy, radiotherapy, immunotherapy, surgical therapy or gene therapy and may be employed in combination with the inhibitor of gene expression therapy, anticancer therapy, or both the inhibitor of gene expression therapy and the anti-cancer therapy, as described herein.

1. Chemotherapy

Examples of chemotherapeutic agents that may be used include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegal1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dronanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine,plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation, and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates (ADCs) comprise monoclonal antibodies (MAbs) that are covalently linked to cell-killing drugs and may be used in combination therapies. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. Exemplary ADC drugs include ADCETRIS® (brentuximab vedotin) and KADCYLA® (trastuzumab emtansine or T-DM1).

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include immune adjuvants, e.g., *Mycobacterium bovis, Plasmodium falciparum*, dinitrochlorobenzene, and aromatic compounds); cytokine therapy, e.g., interferons α, β, and γ, IL-1, GM-CSF, and TNF; gene therapy, e.g., TNF, IL-1, IL-2, and p53; and monoclonal antibodies, e.g., anti-CD20, anti-ganglioside GM2, and anti-p185. It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies. Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody that may be used. Pembrolizumab, also known as MK-3475, Merck 3475, lambrolizumab, KEYTRUDA®, and SCH-900475, is an exemplary anti-PD-1 antibody. CT-011, also known as hBAT or hBAT-1, is also an anti-PD-1 antibody. AMP-224, also known as B7-DCIg, is a PDL2-Fc fusion soluble receptor.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. An exemplary anti-CTLA-4 antibody is ipilimumab (also known as 10D1, MDX-010, MDX-101, and Yervoy®) or antigen binding fragments and variants thereof. In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin.

IV. Kits

In various aspects of the embodiments, a kit is envisioned containing therapeutic agents and/or other therapeutic and delivery agents. In some embodiments, the present embodiments contemplates a kit for preparing and/or administering a kinase inhibitor composition of the embodiments. The kit may comprise one or more sealed vials containing any of the pharmaceutical compositions of the present embodiments. The kit may include, for example, kinase inhibitors as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Driver Kinase Screen

A kinase overexpression screen was performed in vivo in order to identify novel drivers of brain metastasis (FIG. 1). An assay was performed to determine whether the kinases enhanced the growth of brain metastasis. Of 17 kinase pools screened, 14 decreased mouse survival by at least 20%.

To perform the screen, retroviral plasmids encoding activated kinase open reading frames (ORFs) were stably overexpressed in MDA-MB-2131 triple negative breast parental cancer cells (231p) and the cells were injected into the carotid artery of immunocompromised mice. MDA-MB-231 parental cells expressing luciferase, GFP, and pools of up to 24 kinases (231p.luciferase.GFP) were mixed with 231p cells expressing TdTomato and an empty pWZL-Neo-Myr-Flag-DEST vector (231p.TdTomato). Cells were mixed at a 3:1 ratio of kinase pool:vector and $2 \times 10^6$ cells were injected into the carotid artery of nude mice.

When animals displayed neurological symptoms and their heads were determined to be extremely luciferase-positive by IVIS, mice were sacrificed and brain lesions isolated using a dissecting microscope based on GFP-positivity. Portions of the lesions were subjected to direct RNA extraction, while the remainder was dissociated and the cells cultured in vitro as passage 0. gDNA was extracted from the recovered cells and kinase vector sequences amplified by targeted PCR. This DNA was sequenced by MiSeq, yielding a quantitative readout of in vivo selection.

Tumor cells were isolated from the fast-growing brain metastasis and next-generation sequencing (NGS) was performed in order to determine which kinases were responsible for the accelerated growth of brain metastasis, and 24 kinases were identified that are enriched in vivo (Table 1). Because the screen was performed in a pooled overexpression format to simulate heterogeneity in human cancers, it was next validated that the individual kinases identified by enrichment indeed can accelerate the growth of brain metastasis using in vivo gain-of-function experimental brain metastasis assays.

Figure 3A:
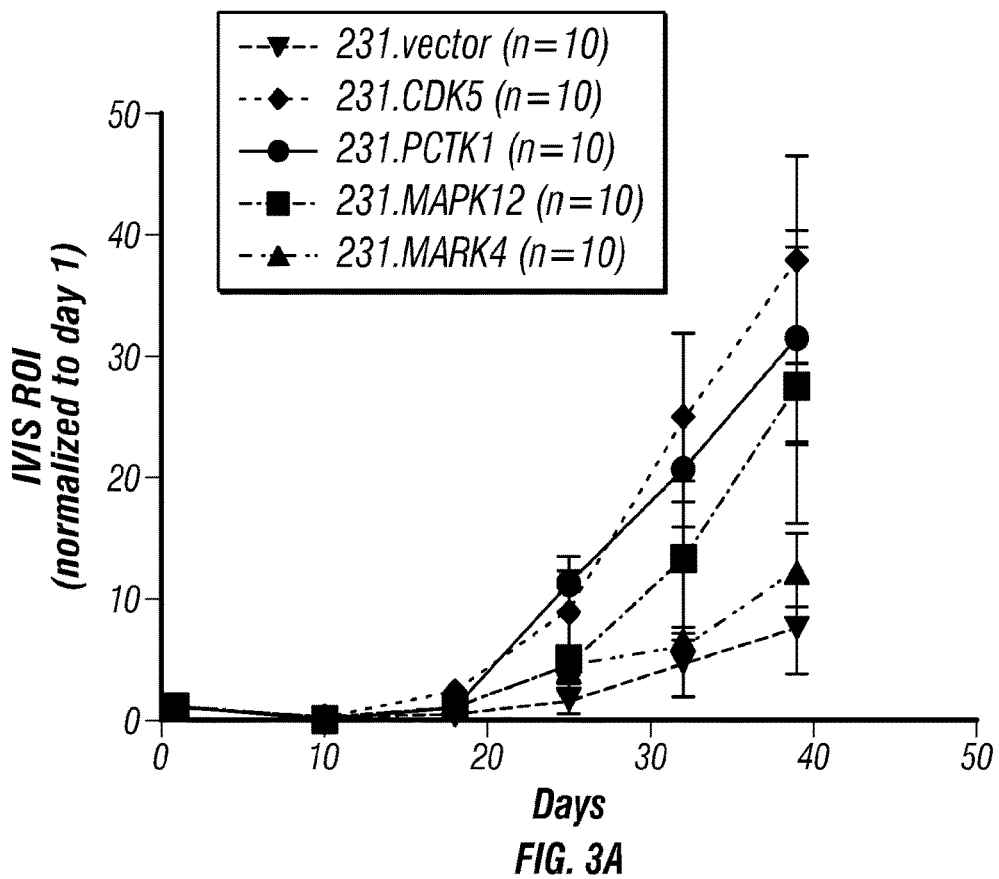
FIGS. 3A-3B: Validation of kinase overexpression-driven brain metastasis growth in vivo. In vivo imaging system (IVIS) was used to quantify the luminescence signal generated by the luciferase-expressing cancer cells. $1 \times 10^5$ cells were injected per animal on day 0 and the luciferase signal was normalized to day 1. (A) Comparison of CDK5-, PCTK1-, MAPK12-, and MARK4-overexpressing brain metastasis growth with corresponding vector controls shows that all kinases except MARK4 are validated drivers of brain metastasis. (B) Comparison of SPHK1-overexpressing cancer cells with vector control cells shows that SPHK1 indeed enhances brain metastasis growth.
Figure 3B:
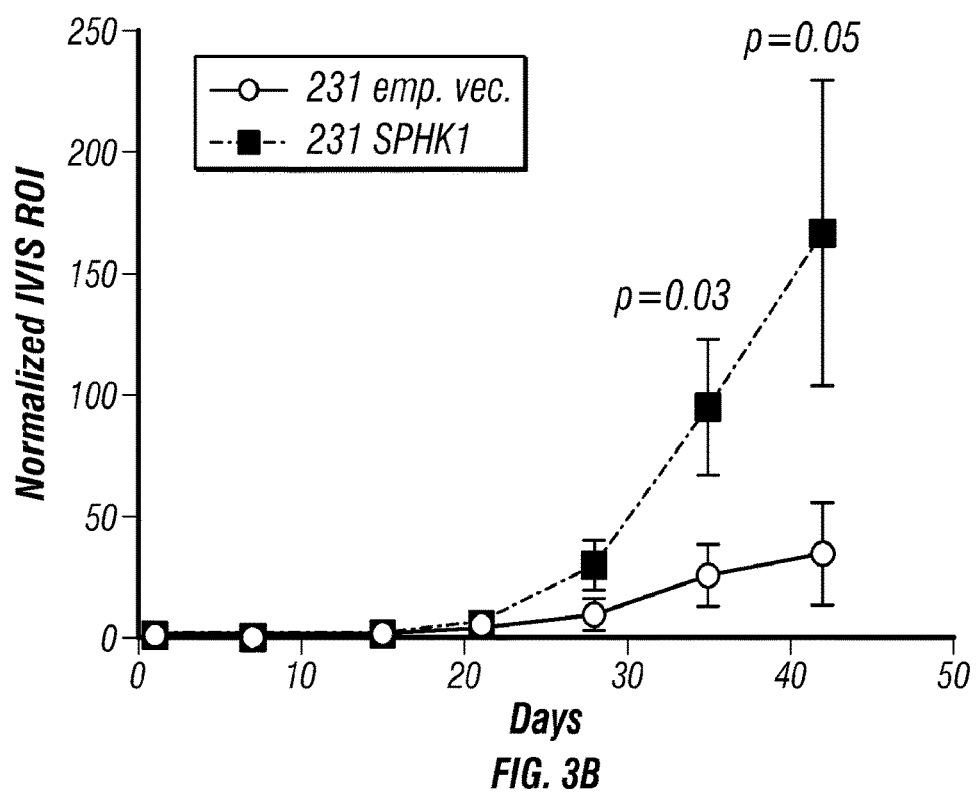

Some of the newly identified kinases were singly overexpressed in luciferase-labeled MDA-MB-231 parental cells. The growth of kinase overexpressing brain metastases was analyzed relative to vector control cells (FIG. 3). In vivo imaging system (IVIS) was used to quantify the luminescence signal generated by the luciferase-expressing cancer cells. $1 \times 10^5$ cells were injected per animal on day 0 and the luciferase signal was normalized to day 1. It was validated that CDK5, PCTKI, MAPK12, LIMK2 and SPHK, all significantly enhanced the growth of brain metastases, while MARK4 caused no significant growth advantage (i.e., not a functional hit as a single kinase).

Figure 4A:
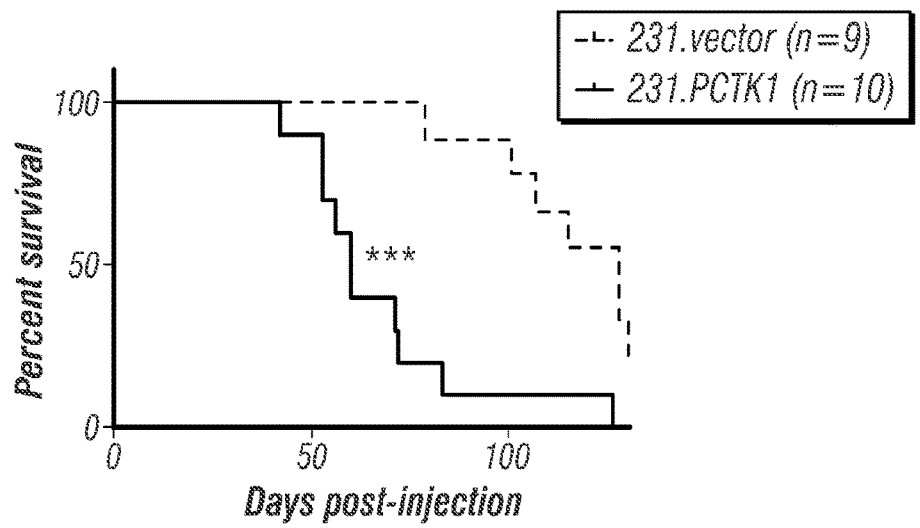
FIGS. 4A-4C: Kinase overexpression in MDA-MB-231 significantly shortens survival in experimental brain metastasis model. Mice injected with kinase overexpression cells or corresponding vector cells were compared for their brain metastasis-specific survival. (A) PCTK1 overexpression shortened survival from a median time of 128 days to 60 days. Survival curves were significantly different (p=0.0004) according to Mantel-Cox log-rank test. (B) SPHK1 overexpression shortened survival from a median time of 131 days to 102.5 days. (C) CDK5 overexpression shortened survival from a median time of 128 days to 70 days.
Figure 4B:
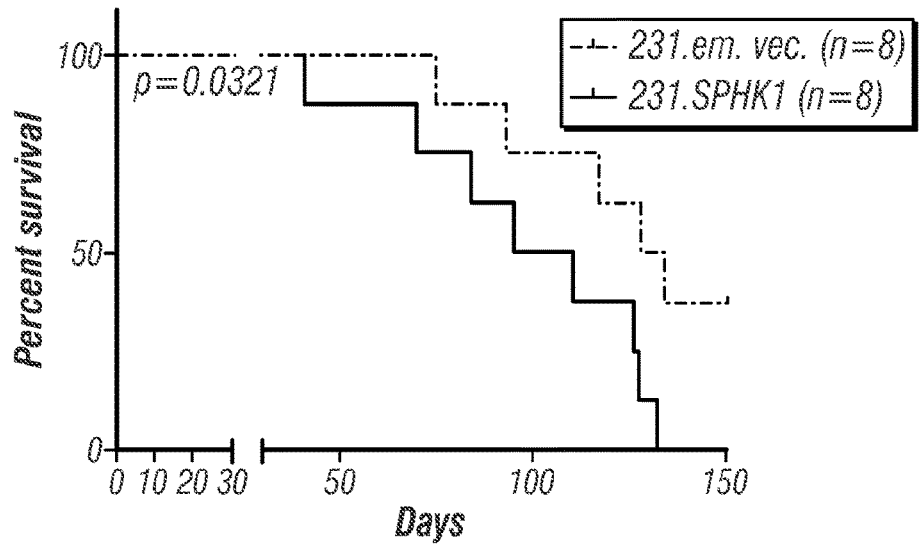
Figure 4C:
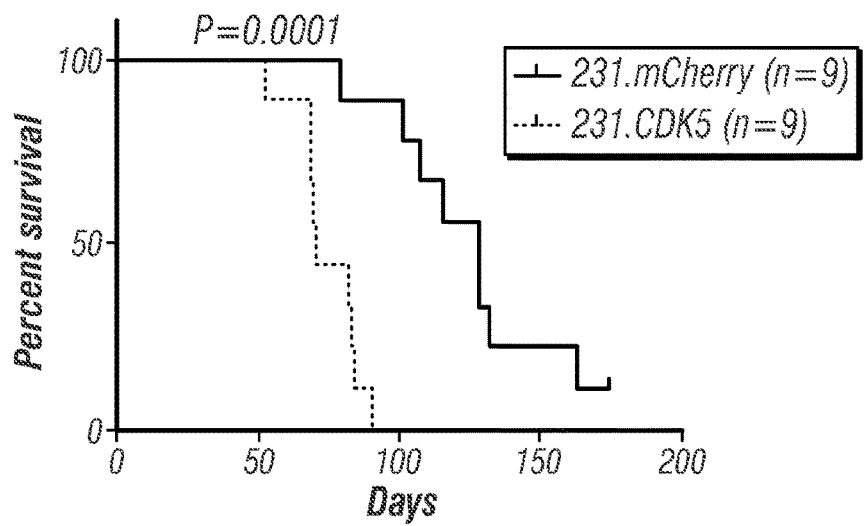

Mice injected with kinase overexpression cells or corresponding vector cells were compared for their brain metastasis-specific survival. PCTK1 overexpression shortened survival from a median time of 128 days to 60 days (FIG. 4A). Survival curves were significantly different (p=0.0004) according to Mantel-Cox log-rank test. SPHK1 overexpression shortened survival from a median time of 131 days to 102.5 days (FIG. 4B). CDK5 overexpression shortened survival from a median time of 128 days to 70 days (FIG. 4C).

Figure 5B:
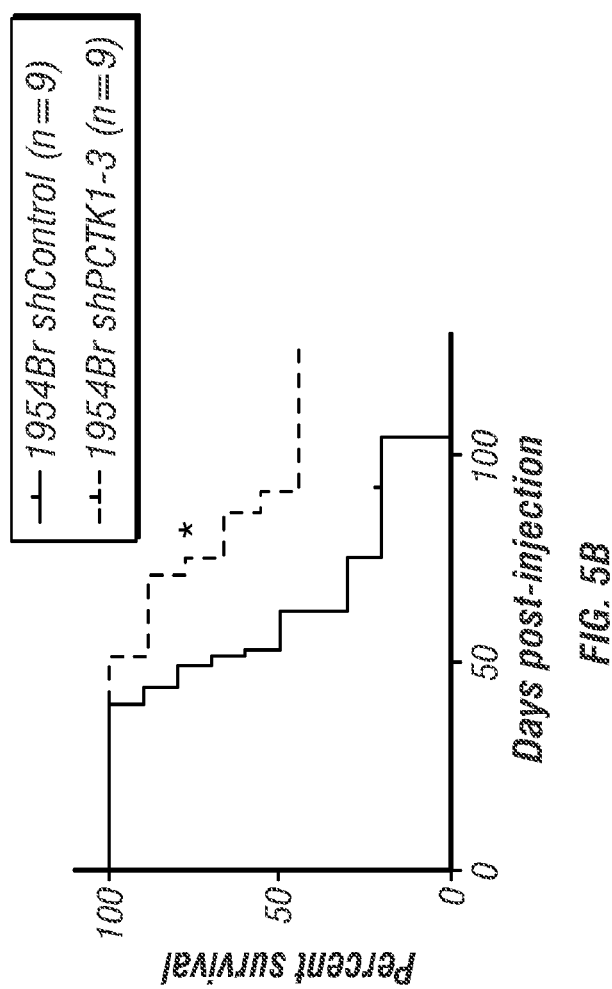
FIGS. 5A-5B: PCTK1 knockdown significantly delays mortality in HCC1954Br model of experimental brain metastasis. (A) Western blot showing shRNA-mediated knockdown efficiency of PCTK1 prior to intracarotid injection. (B) Survival analysis of nude mice injected with $1 \times 10^5$ cells shows that PCTK1 knockdown extends median survival from 57.5 to 91 days.
Figure 5A:
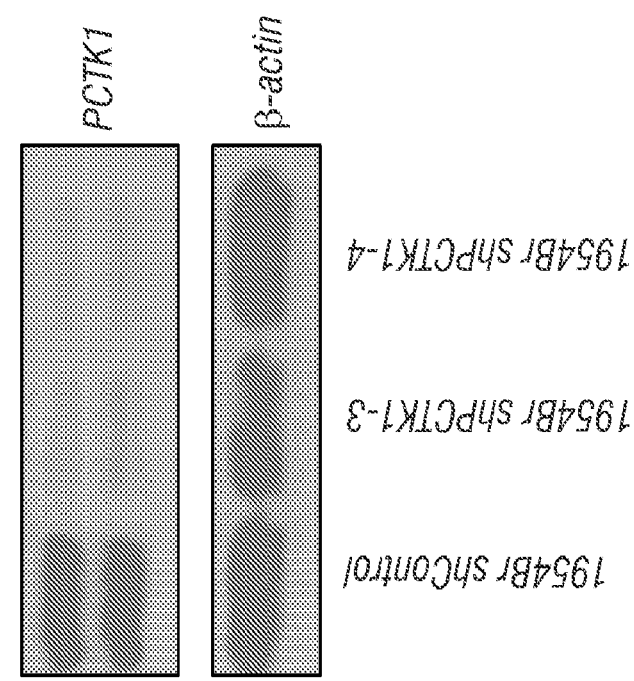

In order to test the therapeutic potential of the newly identified kinase drivers of brain metastatic growth, loss-of-function experimental brain metastasis assays on four of the genes, PCTK.1, SPHK.1, and CDK5. For PCTK1, the PCTK1 gene was stably knocked down by shRNA in the HCC1954.Br brain-seeking line, a HER2-positive line that forms aggressive brain metastasis and has high endogenous PCTKI expression. The PCTK1-knockdown HCC1954.Br cells and control shRNA-transduced HCC1954.Br cells were injected intracarotidly into nude mice respectively, and the two groups of mice were compared for survival. PCTK1 knockdown group had a significantly extended median survival time from 57.5 days to 91 days relative to the vector control shRNA group (FIG. 5B).

For SPHK.1, the highly aggressive brain metastatic line MDA-MB-435 was chosen because it has high endogenous SPHK1 expression. Following stable shRNA-mediated knockdown of SPHK.1, mice injected with the SPHK.1 knockdown cells were compared for experimental brain metastasis-driven mortality relative to mice injected with control MDA-MB-435 cells. Indeed, SPHK1 knockdown extended median mouse survival from 57.5 to 77 days, relative to controls (FIG. 6B). Thus, it was clearly demonstrated that targeting two of the brain metastasis-driver kinases, PCTKI and SPHK1, effectively inhibited brain metastasis and prolonged the survival of mice bearing brain metastasis.

Figure 7A:
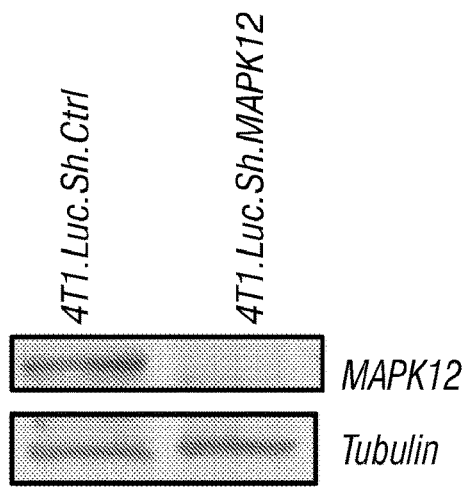
FIGS. 7A-7C: MAPK12 knockdown significantly delays brain metastasis growth at early stages in 4T1 model of experimental brain metastasis. (A) Western blot showing shRNA-mediated knockdown efficiency of MAPK12 prior to intracarotid injection. (B) Comparison of MAPK12-knockdown cancer cells with vector control cells shows that MAPK12 knockdown delays brain metastasis growth. (C) Survival analysis of BALB/c mice injected with 4T1 cells shows that MAPK12 knockdown extends median survival from 15 to 19 days. Survival curves were significantly different (p=0.02) according to Mantel-Cox log-rank test.
Figure 7B:
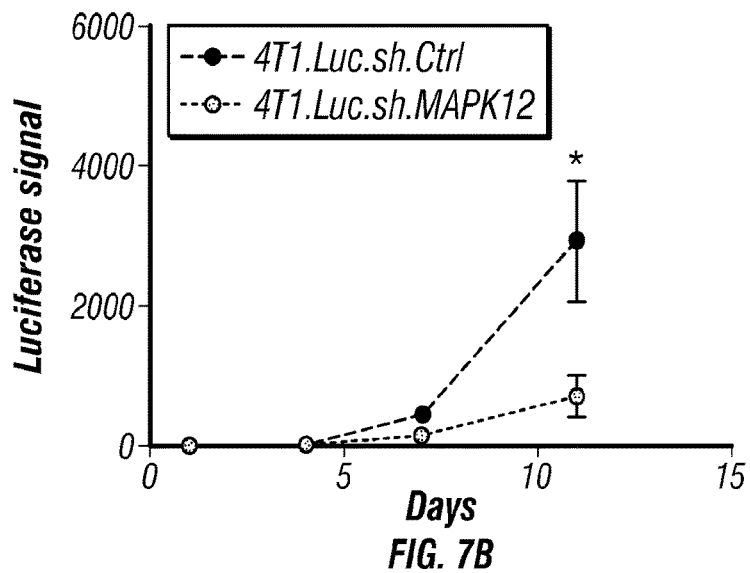
Figure 7C:
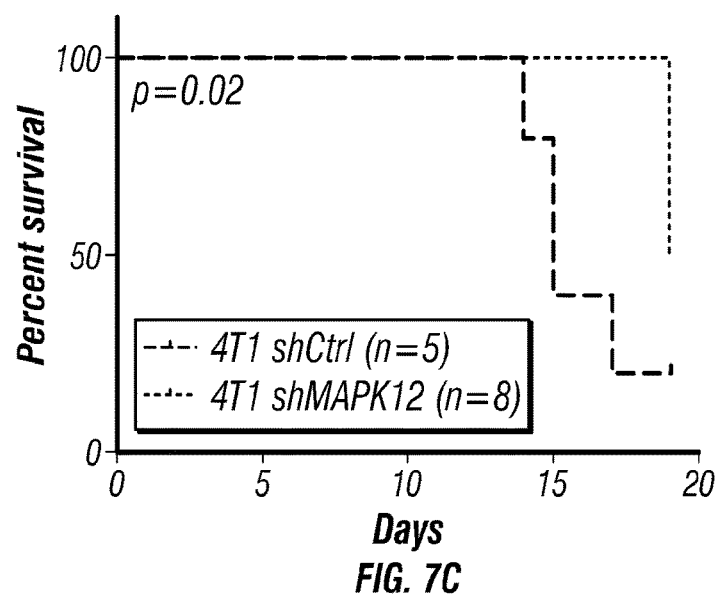

Further, it was found that MAPK12 knockdown significantly delays brain metastasis growth at the early stages in the 4T1 model of experimental brain metastasis. A comparison of MAPK12-knockdown cancer cells with vector control cells showed that MAPK12 knockdown delayed brain metastasis growth (FIG. 7B). In vivo imaging system (IVIS) was used to quantify the luminescence signal generated by the luciferase-expressing cancer cells. $1 \times 10^5$ cells were injected per animal in Balb/c immuno-competent mouse model. (C) Survival analysis of BALB/c mice injected with 4T1 cells showed that MAPK12 knockdown extended median survival from 15 to 19 days (FIG. 7C).

Figure 8A:
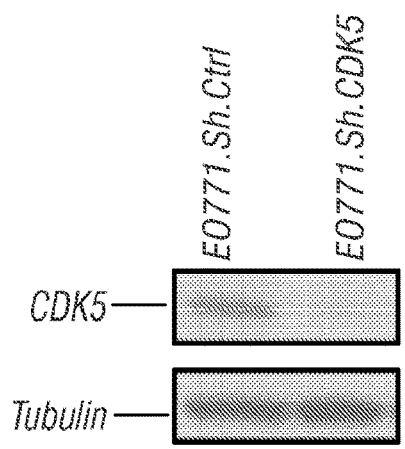
FIGS. 8A-8D: CDK5 knockdown decrease cell proliferation in vitro in hypoxia condition and significantly delays mortality in EO771 model of experimental brain metastasis in CD8 T-cell dependent manner. (A) Western blot showing shRNA-mediated knockdown efficiency of CDK5 in EO771 cells. (B) MTT assays demonstrated a significant decrease in in vitro cell proliferation in CDK5 knockdown cells in hypoxia condition, when compared to vector control cells. (C) Survival analysis of C57BL/6 mice injected with EO771 cells shows that CDK5 knockdown extends median survival from 19 to 23.5 days. (D) Survival analysis of C57BL/6 mice injected with either control or CDK5 knockdown EO771 cells shows that, there is no significant difference in mice survival between these two groups when CD8-T cells were depleted using αCD8 antibody.
Figure 8B:
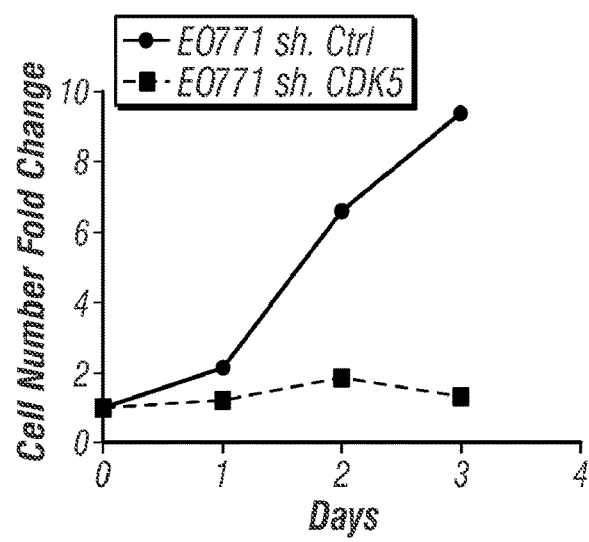
Figure 8C:
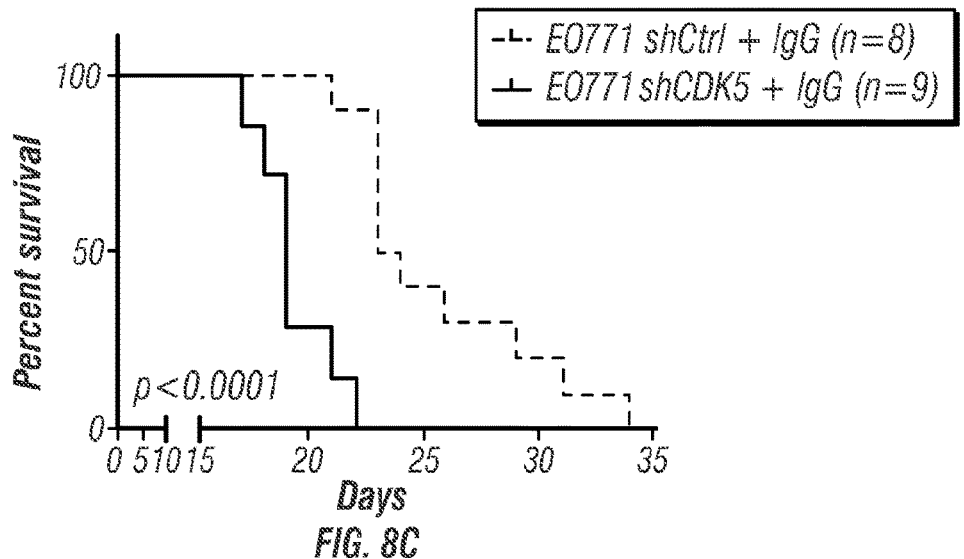
Figure 8D:
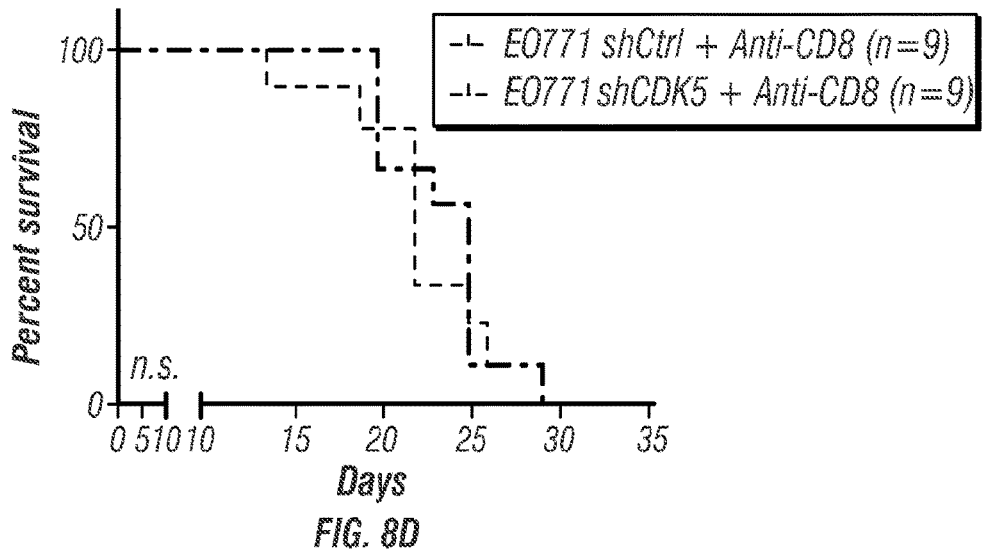

Additionally, CDK5 knockdown decreased cell proliferation in vitro in hypoxia conditions and significantly delayed mortality in EO771 model of experimental brain metastasis in a CD8 T-cell dependent manner. MTT assays demonstrated a significant decrease in in vitro cell proliferation in CDK5 knockdown cells in hypoxia condition, when compared to vector control cells (FIG. 8B). Survival analysis of C57BL/6 mice injected with EO771 cells showed that CDK5 knockdown extended median survival from 19 to 23.5 days (FIG. 8C). Survival analysis of C57BL/6 mice injected with either control or CDK5 knockdown EO771 cells showed that, there was no significant difference in mice survival between these two groups when CD8-T cells were depleted using αCD8 antibody, suggesting that CDK5-driven brain metastasis is partially mediated through the immune system, especially the adaptive T cell compartment (FIG. 8D).

Figure 9A:
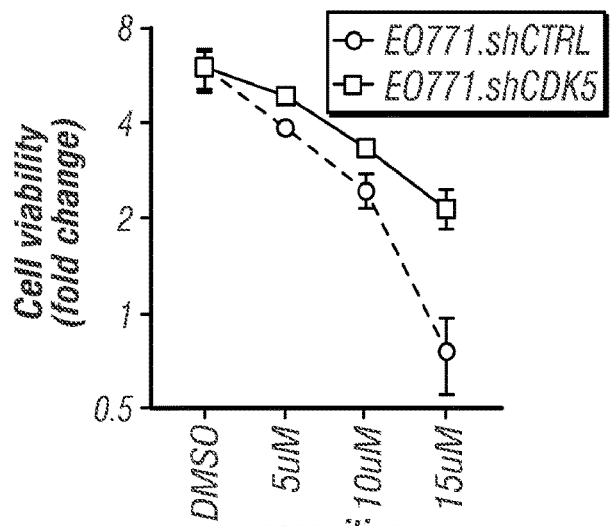
FIGS. 9A-9B: CDK5 knockdown in EO771 cells makes them less sensitive to Roscovitine and more sensitive to T cell cytotoxicity. (A) Cell viability curve demonstrating that CDK5 knockdown in EO771 cells makes them less sensitive to roscovitine, a CDK5 inhibitor, compared to control cells. (B) Cytotoxic T cell killing assay showed that CDK5 knockdown in E0771 cells are more sensitive to activated T cells cytotoxicity compared to EO771 control cells. T cells were activated by CD3/CD28 antibody (100 ng/mL) and IL-2 (10 ng/mL) before co-culturing with tumor cells.
Figure 9B:
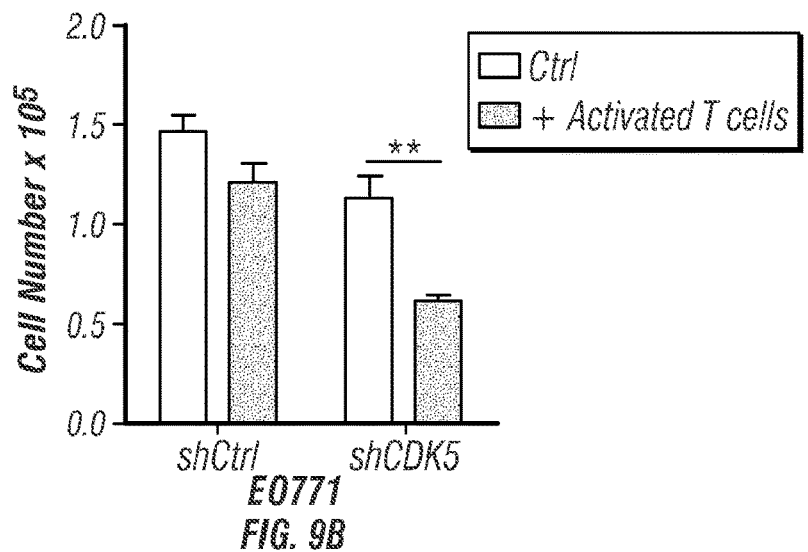

CDK5 knockdown in EO771 cells made them less sensitive to Roscovitine and more sensitive to T cell cytotoxicity. CDK5 knockdown in EO771 cells rendered them less sensitive to roscovitine, a CDK5 inhibitor, compared to control cells (FIG. 9A). A cytotoxic T cell killing assay showed that CDK5 knockdown in EO771 cells were more sensitive to activated T cells cytotoxicity compared to EO771 control cells (FIG. 9B). T cells were activated by CD3/CD28 antibody (100 ng/mL) and IL-2 (10 ng/mL) before co-culturing with tumor cells.

Figure 10A:
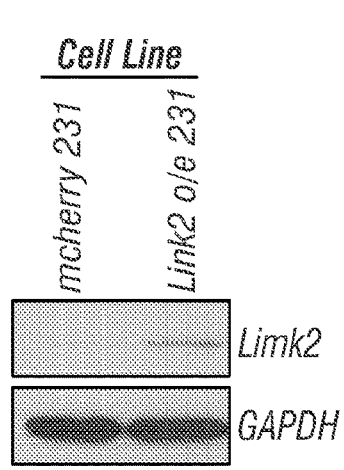
FIGS. 10A-10B: LIMK2 overexpression promotes cell proliferation in vitro in hypoxia condition. (A) Western blot showing overexpression efficiency of LIMK2 in MDA-MB-231 cells. (B) MTT assays demonstrated a significant increase in in vitro cell proliferation in hypoxia condition when LIMK2 is overexpressed, compared to vector control cells.
Figure 10B:
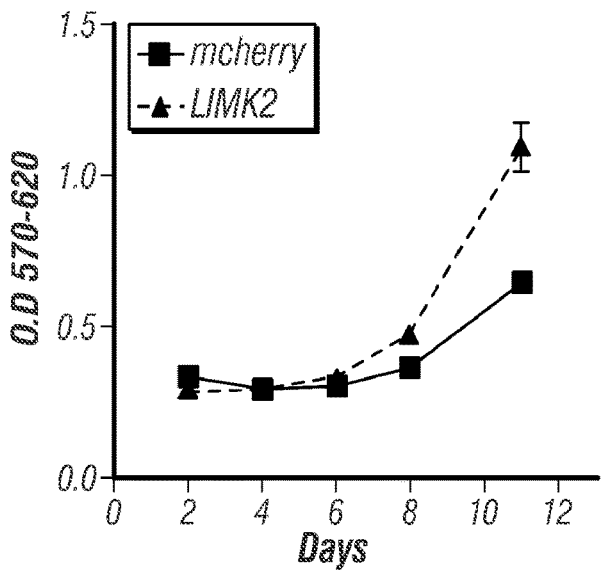
Figure 11C:
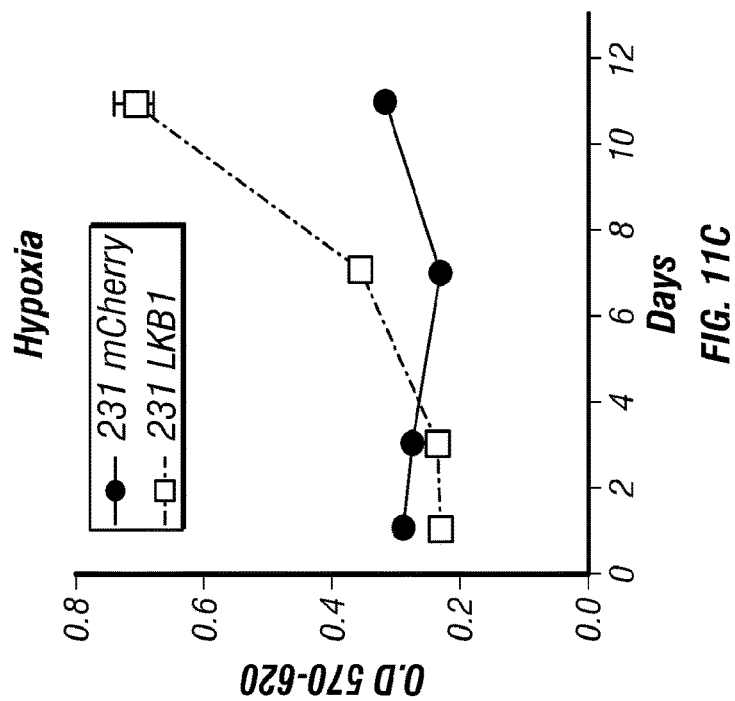
FIGS. 11A-11C: LKB1 overexpression promotes cell proliferation in vitro, both in normoxia and hypoxia condition. (A) Western blot showing overexpression efficiency of LKB1 in MDA-MB-231 cells. (B) MDA-MB-231 cells overexpressed with LKB1 demonstrated a significant increase in in vitro cell proliferation in normoxia condition when compared to vector control cells as shown my MTT assay. (C) MDA-MB-231 cells overexpressed with LKB1 demonstrated a significant increase in in vitro cell proliferation in hypoxia condition when compared to vector control cells as shown my MTT assay.
Figure 11B:
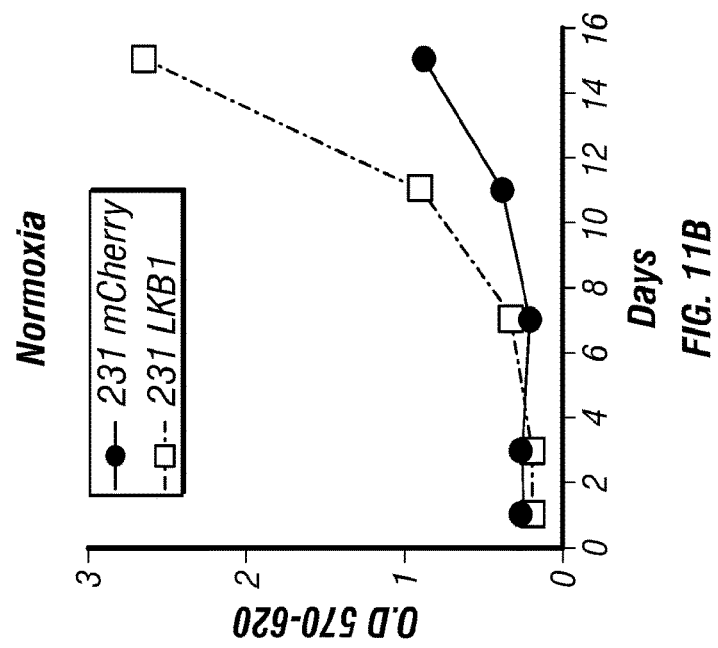
Figure 11A:
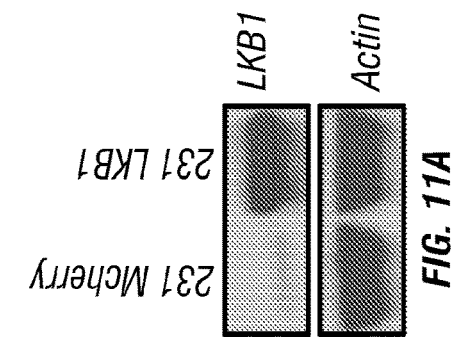

Finally, LIMK2 overexpression promoted cell proliferation in vitro in hypoxia condition. MTT assays demonstrated a significant increase in in vitro cell proliferation in hypoxia conditions when LIMK2 was overexpressed, compared to vector control cells (FIG. 10B). MDA-MB-231 cells overexpressed with LKB1 demonstrated a significant increase in in vitro cell proliferation in hypoxia condition when compared to vector control cells as shown my MTT assay (FIG. 11B).

Therefore, inhibition of the kinases identified by the screen significantly delay brain metastasis-related mortality and are effective therapeutic targets for brain metastasis.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Boonsri et al., *Biochem Biophys Res Commun.* 430(1):313-9, 2012.
Cane et al., *Science* 282:63, 1998.
Cweik et al., *Oncotarget*, 6(1):116-29, 2015.
Hoessel et al., *Nature Cell Biology*, 60-67, 1999.
International Patent Publication No. WO1995001994
International Patent Publication No. WO1998042752
International Patent Publication No. WO2000037504
International Patent Publication No. WO2001/14424
International Patent Publication No. WO2001014424
International Patent Publication No. WO2009/101611
International Patent Publication No. WO2009/114335
International Patent Publication No. WO2010/027827
International Patent Publication No. WO2011/066342
International Patent Publication No. WO2015016718
Malami et al., *Molecules*, 21(4):417, 2016.
U.S. Pat. No. 4,870,287
U.S. Pat. No. 5,760,395
U.S. Pat. No. 5,844,905
U.S. Pat. No. 5,885,796
U.S. Pat. No. 6,207,156
U.S. Pat. No. 6,673,611
U.S. Pat. No. 8,008,449
U.S. Pat. No. 8,017,114
U.S. Pat. No. 8,119,129
U.S. Pat. No. 8,329,867
U.S. Pat. No. 8,354,509
U.S. Pat. No. 8,372,888
U.S. Pat. No. 8,735,553
U.S. Patent Publication No. 20040019001
U.S. Patent Publication No. 20110008369
U.S. Patent Publication No. 2014022021
U.S. Patent Publication No. 20140294898

What is claimed is:

1. A method for inhibiting brain metastasis in a subject having a cancer comprising administering an effective amount of a kinase inhibitor to the subject, wherein the kinase inhibitor targets a kinase selected from the group consisting of ADCK4, BTK, CAMK4, CDK5, CDK5R1, CLK3, LIMK2, PAK4, PMVK, PRKACB, PRKACG, PRKCI, TSSK6, and ZC3HC1, wherein the cancer is breast cancer or lung cancer and wherein the kinase inhibitor is not ridaura.

2. The method of claim 1, wherein the breast cancer is further defined as triple negative breast cancer.

3. The method of claim 1, wherein the subject was not known to have brain metastasis prior to treatment.

4. The method of claim 1, wherein the subject was known to have one or more brain metastasis prior to treatment.

5. The method of claim 1, wherein the kinase inhibitor is siRNA or miRNA.

6. The method of claim 1, wherein the kinase inhibitor is a selective pharmacological inhibitor.

7. The method of claim 1, wherein the kinase inhibitor of CDK5 is dinaciclib, indirubin, (S)-CR8, kenpaullone, PHA-793887, AT7519, roscovitine, milciclib, SNS-032, or olomoucine.

8. The method of claim 1, wherein the kinase inhibitor of LIMK2 is BMS-5, Pyr-1, or T56-LIMKi.

9. The method of claim 1, wherein the kinase inhibitor of BTK is ibrutinib, acalabrutinib, ONO-4059, spebrutinib, BGB-3111, or HM71224.

10. The method of claim 1, wherein the kinase inhibitor of CAMK4 is KN-93.

11. The method of claim 1, wherein the kinase inhibitor of PMVK is CDDD_1633, CSDDD_2260, CSDDD_2419, or luteolin.

12. The method of claim 1, wherein the kinase inhibitor of PRKCI is RXDX-108.

13. The method of claim 1, wherein the kinase inhibitor is administered intrathecally or intranasally.

14. The method of claim 1, further comprising administering at least a second therapeutic agent.

15. The method of claim 14, wherein the second therapeutic agent is radiation therapy, chemotherapy, immunotherapy, and/or metabolic modulation.

16. The method of claim 14, wherein the second therapeutic agent is administered concurrently with the kinase inhibitor.

17. The method of claim 14, wherein the second therapeutic agent is administered sequentially with the kinase inhibitor.

18. The method of claim 1, wherein the kinase is CDK5.
19. The method of claim 1, wherein the kinase is LIMK2.
20. The method of claim 1, wherein the kinase is BTK.
21. The method of claim 1, wherein the kinase is CAMK4.
22. The method of claim 1, wherein the kinase is PMVK.
23. The method of claim 1, wherein the kinase is ADCK4.
24. The method of claim 1, wherein the kinase is CLK3.
25. The method of claim 1, wherein the kinase is PAK4.
26. The method of claim 1, wherein the kinase is PRKACB.
27. The method of claim 1, wherein the kinase is PRKACG.
28. The method of claim 1, wherein the kinase is TSSK6.
29. The method of claim 1, wherein the kinase is ZC3HC1.
30. The method of claim 18, wherein the kinase inhibitor of CDK5 is roscovitine.
31. The method of claim 18, wherein the kinase inhibitor of CDK5 is dinaciclib.
32. The method of claim 18, wherein the kinase inhibitor of CDK5 is indirubin.
33. The method of claim 18, wherein the kinase inhibitor of CDK5 is (S)-CR8.
34. The method of claim 18, wherein the kinase inhibitor of CDK5 is kenpaullone, PHA-793887, AT7519, milciclib, SNS-032, or olomoucine.
35. The method of claim 1, wherein the kinase inhibitor targets a kinase selected from the group consisting of ADCK4, BTK, CAMK4, CDK5, CDK5R1, CLK3, LIMK2, PAK4, PMVK, PRKACB, PRKACG, TSSK6, and ZC3HC1.

* * * * *